US012383635B2

(12) United States Patent
Chen et al.

(10) Patent No.: US 12,383,635 B2
(45) Date of Patent: *Aug. 12, 2025

(54) RADIOLABELLED MGL PET LIGANDS

(71) Applicant: Janssen Pharmaceutica NV, Beerse (BE)

(72) Inventors: Gang Chen, San Diego, CA (US); Chaofeng Huang, San Diego, CA (US); Jimmy T. Liang, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,575

(22) Filed: Dec. 1, 2023

(65) Prior Publication Data
US 2024/0100198 A1 Mar. 28, 2024

Related U.S. Application Data

(63) Continuation of application No. 17/036,919, filed on Sep. 29, 2020, now Pat. No. 11,839,663.

(60) Provisional application No. 62/907,852, filed on Sep. 30, 2019.

(51) Int. Cl.
*A61K 51/04* (2006.01)
*C07D 471/04* (2006.01)

(52) U.S. Cl.
CPC ........ *A61K 51/0455* (2013.01); *C07D 471/04* (2013.01)

(58) Field of Classification Search
CPC .............. A61K 51/0455; C07D 471/04; C07B 2200/05
USPC ....................................................... 424/1.89
See application file for complete search history.

(56) References Cited

U.S. PATENT DOCUMENTS

| | | | |
|---|---|---|---|
| 4,812,462 A | 3/1989 | Blankley et al. |
| 4,816,463 A | 3/1989 | Blankley et al. |
| 5,338,744 A | 8/1994 | Dudley et al. |
| 8,431,704 B2 | 4/2013 | Love et al. |
| 8,513,248 B2 | 8/2013 | Dean et al. |
| 8,871,760 B2 | 10/2014 | Brotherton-pleiss et al. |
| 8,933,236 B2 | 1/2015 | Chowdhury et al. |
| 8,987,249 B2 | 3/2015 | Anderskewitz et al. |
| 9,040,534 B2 | 5/2015 | Ameriks et al. |
| 9,056,874 B2 | 6/2015 | Adams et al. |
| 9,066,946 B2 | 6/2015 | Alcazar Vaca et al. |
| 9,096,596 B2 | 8/2015 | Alcazar Vaca et al. |
| 9,156,824 B2 | 10/2015 | Dally et al. |
| 9,181,271 B2 | 11/2015 | Li et al. |
| 9,233,974 B2 | 1/2016 | Link et al. |
| 9,242,969 B2 | 1/2016 | Barsanti et al. |
| 9,273,047 B2 | 3/2016 | Hunt et al. |
| 9,273,947 B2 | 3/2016 | Kim et al. |
| 9,290,476 B2 | 3/2016 | Leonard et al. |
| 9,375,418 B2 | 6/2016 | Schmidt et al. |
| 9,434,715 B2 | 9/2016 | Conza et al. |
| 9,447,045 B2 | 9/2016 | Chen et al. |
| 9,464,084 B2 | 10/2016 | Alcazar Vaca et al. |
| 9,532,992 B2 | 1/2017 | Kuntz et al. |
| 9,561,228 B2 | 2/2017 | Haq et al. |
| 9,611,252 B2 | 4/2017 | Mcdonald et al. |
| 9,617,272 B2 | 4/2017 | Kumar et al. |
| 9,637,456 B2 | 5/2017 | Amans et al. |
| 10,112,937 B2 | 10/2018 | Alcazar Vaca et al. |
| 10,150,765 B2 | 12/2018 | Alcazar Vaca et al. |
| 10,150,766 B2 | 12/2018 | Letavic et al. |
| 10,703,749 B2 | 7/2020 | Alcazar Vaca et al. |
| 11,225,478 B2 | 1/2022 | Alcazar Vaca et al. |
| 11,820,770 B2 | 11/2023 | Alcazar Vaca et al. |
| 11,839,663 B2 | 12/2023 | Chen et al. |
| 2004/0214855 A1 | 10/2004 | Carpino et al. |
| 2005/0096345 A1 | 5/2005 | Thompson et al. |
| 2005/0101594 A1 | 5/2005 | Binch et al. |
| 2006/0217448 A1 | 9/2006 | Kelly et al. |
| 2006/0293337 A1 | 12/2006 | Evans et al. |
| 2008/0275052 A1 | 11/2008 | Dhar et al. |
| 2010/0035893 A1 | 2/2010 | Hoornaert |
| 2010/0144758 A1 | 6/2010 | Dillon et al. |
| 2011/0252717 A1 | 10/2011 | Graf Fernandez |
| 2011/0294790 A1 | 12/2011 | Mantegani et al. |
| 2012/0077787 A1 | 3/2012 | Baeschlin et al. |
| 2012/0101081 A1 | 4/2012 | Zhang et al. |
| 2012/0157436 A1 | 6/2012 | Dean et al. |

(Continued)

FOREIGN PATENT DOCUMENTS

| CN | 1823066 A | 8/2006 |
|---|---|---|
| CN | 101778850 A | 7/2010 |

(Continued)

OTHER PUBLICATIONS

Ahn et al., "Enzymatic Pathways That Regulate Endocannabinoid Signaling in the Nervous System", Chem Rev., 2008, p. 1687-1707, vol. 108, No. 5.

Alekseev, et al., Use of the Graebe-Ullmann Reaction in the Synthesis of 8-Methyl-Y-Carboline and Isomeric Aromatic Aza-Y-Carbolines, Chemistry of Heterocyclic Compounds, 2012, pp. 1235-1250, vol. 48 Issue 8.

Alhouayek et al., "Increasing endogenous 2-arachidonoylglycerol levels counteracts colitis and related systemic inflammation", FASEB J., Aug. 2011, 2711-2721, vol. 25, No. 8.

Arbeloa, et al., P2X7 receptor blockade prevents ATP excitotoxicity in neurons and reduces brain damage after ischemia, Neurobiology of Disease, 2012, pp. 954-961, vol. 45.

Arulkumaran, et al., A potential therapeutic role for P2X7 receptor (P2X7R) antagonists in the treatment of inflammatory diseases, Expert Opin Investig, 2011, pp. 897-915, vol. 20 Issue 7.

(Continued)

*Primary Examiner* — Michael G. Hartley
*Assistant Examiner* — Sean R Donohue

(57) ABSTRACT

The present invention relates to novel, selective, radiolabelled compound having monoacylglycerol lipase (MGL) affinity which are useful for imaging and quantifying MGL receptor expression, distribution and enzyme occupancy in tissues, using positron-emission tomography (PET). The invention is also directed to compositions comprising such compounds, the use of such compounds and compositions for imaging a tissue, cells or a host, in vitro or in vivo and to precursors of said compounds.

4 Claims, 2 Drawing Sheets

(56) References Cited

U.S. PATENT DOCUMENTS

| | | |
|---|---|---|
| 2012/0190680 A1 | 7/2012 | Bakthavatchalam et al. |
| 2013/0137672 A1 | 5/2013 | Branstetter et al. |
| 2014/0171430 A1 | 6/2014 | Letavic et al. |
| 2014/0213554 A1 | 7/2014 | Wu et al. |
| 2014/0251902 A1 | 9/2014 | Solheim et al. |
| 2014/0275015 A1 | 9/2014 | Alcazar Vaca et al. |
| 2014/0275056 A1 | 9/2014 | Letavic et al. |
| 2014/0275061 A1 | 9/2014 | Orwat et al. |
| 2014/0275096 A1 | 9/2014 | Ameriks et al. |
| 2014/0275097 A1 | 9/2014 | Hoveyda et al. |
| 2014/0275120 A1 | 9/2014 | Alcazar Vaca et al. |
| 2015/0029190 A1 | 1/2015 | Ishida et al. |
| 2015/0290190 A1 | 10/2015 | Ameriks et al. |
| 2015/0322062 A1 | 11/2015 | Alcazar Vaca et al. |
| 2016/0016962 A1 | 1/2016 | Ameriks et al. |
| 2016/0024082 A1 | 1/2016 | Alcazar Vaca et al. |
| 2016/0039809 A1 | 2/2016 | Alcazar Vaca et al. |
| 2016/0039836 A1 | 2/2016 | Letavic et al. |
| 2016/0046596 A1 | 2/2016 | Banerjee et al. |
| 2016/0376271 A1 | 12/2016 | Alcazar Vaca et al. |
| 2017/0029390 A1 | 2/2017 | Butler et al. |
| 2017/0081342 A1 | 3/2017 | Cheung et al. |
| 2018/0118749 A1 | 5/2018 | Andres Gil et al. |
| 2018/0327410 A1 | 11/2018 | Grice et al. |
| 2020/0102303 A1 | 4/2020 | Ameriks et al. |
| 2020/0102311 A1 | 4/2020 | Ameriks et al. |
| 2021/0093738 A1 | 4/2021 | Chen et al. |
| 2022/0372030 A1 | 11/2022 | Ameriks et al. |

FOREIGN PATENT DOCUMENTS

| | | |
|---|---|---|
| FR | 2857363 A1 | 1/2005 |
| JP | 2012525351 A | 10/2012 |
| JP | 2013/505220 A | 2/2013 |
| WO | 2004/014374 A1 | 2/2004 |
| WO | 2004013144 A1 | 2/2004 |
| WO | 2006/023750 A2 | 3/2006 |
| WO | 2006/080884 A1 | 8/2006 |
| WO | 2006/110516 A1 | 10/2006 |
| WO | 2009/002423 A2 | 12/2008 |
| WO | 2009/023623 A1 | 2/2009 |
| WO | 2009095253 A1 | 8/2009 |
| WO | 2010124108 A1 | 10/2010 |
| WO | 2010124122 A1 | 10/2010 |
| WO | 2010/125101 A1 | 11/2010 |
| WO | 2010/125102 A1 | 11/2010 |
| WO | 2011050202 A1 | 4/2011 |
| WO | 2011/103715 A1 | 9/2011 |
| WO | 2011/121137 A1 | 10/2011 |
| WO | 2012/040048 A2 | 3/2012 |
| WO | 2012054716 A1 | 4/2012 |
| WO | 2012054721 A1 | 4/2012 |
| WO | 2012145581 A1 | 10/2012 |
| WO | 2013055984 A1 | 4/2013 |
| WO | 2014/152589 A1 | 9/2014 |
| WO | 2014/152621 A1 | 9/2014 |
| WO | 2014152604 A1 | 9/2014 |
| WO | 2014/154897 A1 | 10/2014 |
| WO | 2015/025026 A1 | 2/2015 |
| WO | 2016/039977 A1 | 3/2016 |
| WO | 2016/039983 A1 | 3/2016 |
| WO | 2016040789 A1 | 3/2016 |
| WO | 2016158956 A1 | 10/2016 |
| WO | 2017087858 A1 | 5/2017 |
| WO | 2018085148 A1 | 5/2018 |
| WO | 2018112312 A1 | 6/2018 |
| WO | 2018134698 A1 | 7/2018 |
| WO | 2020065613 A1 | 4/2020 |
| WO | 2020065614 A1 | 4/2020 |
| WO | 2020211798 A1 | 10/2020 |
| WO | 2021064569 A1 | 4/2021 |
| WO | 2021/191359 A1 | 9/2021 |

OTHER PUBLICATIONS

Avignone, et al., Status Epilepticus Induces a Particular Microglial Activation State Characterized by Enhanced Puriergic Signaling, The Journal of Neuroscience, Sep. 10, 2008, pp. 9133-9144, vol. 28 Issue 37, Society for Neuroscience.

Bagshawe, "Antibody-Directed Enzyme prodrug Therapy : A Review", Drug Development Research, , vol. 34; pp. 220-230 (1995).

Bartlett, et al., The P2X7 Receptor Channel: Recent Development and the use of P2X7 antagonists in model of Disease, Pharmocol Rev, 2014, pp. 638-675, vol. 66.

Basso, et al., Behavioral profile of P2X7 receptor knockout mice in animal models of depression and anxiety: Relevance for neuropsychiatric disorders, Behavioural Brain Research, Oct. 18, 2008, pp. 83-90, vol. 198, Elsevier B.V.

Bedse et al., "Functional Redundancy Between Canonical Endocannabinoid Signaling Systems in the Modulation off Anxiety", Biol Psychiatry, Oct. 1, 2017, 488-499, vol. 82, No. 7.

Bedse et al., "Therapeutic endocannabinoid augmentation for mood and anxiety disorders: comparative profiling of FAAH, MAGL and dual inhibitors", Transl Psychiatry, Apr. 26, 2018, 92, vol. 8, No. 1.

Benito et al., "Cannabinoid CB2 Receptors in Human Brain Inflammation", British Journal of Pharmacology, 2008, 277-285, vol. 153.

Bennet, et al. (Editor), "Part XIV Oncology", Cecil Textbook of Medicine, vol. 1, 20th Edition: pp. 1004-1010 (1996).

Berge, S.M. et al., "Pharmaceutical Salts", J. Pharm. Sci., 1977, pp. 1-19, vol. 66 Issue 1.

Bernal-Chico et al., "Blockade of monoacylglycerol lipase inhibits oligodendrocyte excitotoxicity and prevents demyelination in vivo", Glia, Jan. 2015, 163-176, vol. 63, No. 1.

Bertolini, et al., "A New Rational Hypothesis for the Pharmacophore of the Active Metabolite of Leflunomide, a Potent Immunosuppressive Drug", Journal of Medicinal Chemistry, vol. 40 (13); pp. 2011-2016 (1997).

Bourzac, et al., Glucose Transporter 2 Expression is Down Regulated Following P2X7 Activation in Enterocytes, Journal of Cellular Physiology, 2013, pp. 120-129, vol. 228.

Buczynski and Parsons, "Quantification of brain endocannabinoid levels: methods, interpretations and pitfalls". Brit J Pharmacol, 2010, 423-442, vol. 160, No. 3.

Bundgaard, Hans "Design of Products", Design of Products, pp. 1-3, (1985).

Capuron, et al., Immune system to brain signaling: Neuropsychopharmacological implications, Pharmacology & Therapeutics, 2011, pp. 226-238, vol. 130, Elsevier Inc.

Carroll et al., "Synthesis and Pharmacological Characterization of Nicotinic Acetylcholine Receptor Properties of (+)- and (−)-Pyrido-[3,4-b]homotropanes", Journal of Medicinal Chemistry, 2006, 3244-3250, vol. 49, No. 11.

Cavuoto et al., "The Expression of Receptors for Endocannabinoids in Human and Rodent Skeletal Muscle", Biochemical and Biophysical Research Communications, 2007, 105-110, vol. 364.

Chen et al., "Monoacylglycerol Lipase Is a Therapeutic Target for Alzheimer's Disease", Cell Rep., Nov. 29, 2012, 1329-1339, vol. 2, No. 5.

Chessell, et al., Disruption of the P2X7 purinoceptor gene abolishes chronic inflammatory and neuropathic pain, Pain, Jan. 5, 2005, pp. 386-396, vol. 114, Elsevier B.V.

Chinnadurai et al., "Monoacylglycerol lipase inhibition as potential treatment for interstitial cystitis", Medical Hypotheses, Oct. 2019, 109321, vol. 131.

Christensen et al., "Efficacy and safety of the weight-loss drug rimonabant: a meta-analysis of randomised trials", The Lancet, 2007, 1706-1713, vol. 370.

Chu, et al., Inhibition of P2X7 receptor ameliorates transient global cerebral ischemia/reperfusion injury via modulating inflammatory responses in the rat hippocampus, Journal of Neuroinflammation, 2012, pp. 1-10, vol. 9 Issue 69.

Considine, G.D., "Van Nostrand's Encyclopedia of Chemistry", 5th Ed, 2005, pp. 261-261, Page number.

Covey et al., "Inhibition of endocannabinoid degradation rectifies motivational and dopaminergic deficits in the Q175 mouse model of Huntington's disease", Neuropsychopharmacology, 2018, 2056-2063, vol. 43.

(56) References Cited

OTHER PUBLICATIONS

Curry et al., "Monoacylglycerol Lipase Inhibitors Reverse Paclitaxel-Induced Nociceptive Behavior and Proinflammatory Markers in a Mouse Model of Chemotherapy-Induced Neuropathy", J Pharmacol Exp Ther., Jul. 2018, 169-183, vol. 366, No. 1.
Dantzer, Robert, Cytokine, Sickness Behavior, and Depression, Immunol Allergy Clin N Am, 2009, pp. 247-264, Volime 29.
Database Chemcats Ambinter Stock Screening Collection Accession No. 2040381923, Feb. 13, 2008.
Database Chemcats Ambinter Stock Screening Collection Accession No. 2040548370, Feb. 13, 2008.
Database Chemcats Ambinter Stock Screening Collection Accession No. 2046454718, Feb. 13, 2008.
Database Chemcats Ambinter Stock Screening Collection Database Accession No. 2040033692, Feb. 13, 2008.
Database Chemcats Aurora Screening Library Accession No. 2037938546, Sep. 6, 2007.
Database Chemcats Enamine Screening Library Accession No. 2035772210, Jan. 17, 2008.
Database Chemcats Ryan Scientific Screening Library Accession No. 2042634059, Jan. 25, 2008.
Database Chemcats Ryan Scientific Screening Library Accession No. 2042637020, Jan. 25, 2008.
Database Chemcats Ryan Scientific Screening Library Accession No. 2042676574, Jan. 25, 2008.
Database Chemcats Ryan Scientific Screening Library Accession No. 2043876860, Jan. 25, 2008.
Database Chemcats Ukrorgsynthesis Screening Collection Accession No. 2033253463, Mar. 6, 2007.
Delarasse, et al., The Purinergic Receptor P2X7 Triggers—Secretasedependent Processing of the Amyloid Precursor Protein, The Journal of Biological Chemistry, Nov. 16, 2010, pp. 2596-2606, vol. 286 Issue 4.
Dermer, Gerald B., "Another Anniversary For the War on Cancer",, Nature Publishing Group, Mar. 12, 1994, p. 320, vol. 12 No 2.,
Devane et al., "Isolation and structure of a brain constituent that binds to the cannabinoid receptor", Science, 1992, 1946-1949, vol. 258.
Di Marzo et al., "Endocannabinoids and the regulation of their levels in health and disease", Curr Opin Lipidol, 2007, 129-140, vol. 18.
Di Marzo et al., "Plant, Synthetic, and Endogenous Cannabinoids in Medicine", Annu Rev Med., 2006, 553-574., vol. 57.
Diaz-Hernandez, et al., Altered P2X7-receptor level and function in mouse models of Huntington's disease and therapeutic efficacy of antagonist administration, The FASEB Journal, 2009, pp. 1893-1906, vol. 23.
Diaz-Hernandez, et al., In vivo P2X7 inhibition reduces amyloid plaques in Alzheimer's disease through GSK3 and secretases, Neurobiology of Aging, 2012, pp. 1816-1828, vol. 33.
Dinh et al., "Brain monoglyceride lipase participating in endocannabinoid inactivation", Proc Natl Acad Sci USA, Aug. 6, 2002, 10819-10824, vol. 99, No. 16.
Donnelly-Roberts, et al., [3H]A-804598 ([3H]2-cyano-1-[(1S)-1-phenylethyl]-3-quinolin-5-yiguanidine) is a novel, potent, and selective antagonist radioligand for P2X7 receptors, Neuropharmacology, 2009, pp. 223-229, vol. 56.
Duan, et al., P2X7 Receptors: Properties and Relevance to CNS Function, GLIA, 2006, pp. 738-746, vol. 54.
Dyatkin et al., Determination of the Absolute Configuration of a Key Tricyclic Component of a Novel Vasopressin Receptor Antagonist by Use of Vibrational Circular Dichroism, Chirality, 2002, pp. 215-219, vol. 14.
Engel, et al., Seizure suppression and neuroprotection by targeting the purinergic P2X7 receptor during status epilepticus in mice, The FASEB Journal, 2012, pp. 1616-1628, vol. 26.
Ferrari, et al., The P2X7 Receptor: A Key Player in IL-1 Processing and Release1, The Journal of Immunology,, 2006, pp. 3877-3883, vol. 176.

Fleisher, et al., "Improved oral drug delivery: solubility limitations overcome by the use of prodrugs", Advanced Drug Delivery Reviews, vol. 19; pp. 115-130 (1996).
Folkes et al., "An endocannabinoid-regulated basolateral amygdala-nucleus accumbens circuit modulates sociability", J Clin Invest., 2020, 1728-1742., vol. 130, Issue 4.
Freshney, et al., Culture of Animal Cells, Manual of Basic Technique, 1983, pp. 1-6, Chapter 1.
Friedle, et al., Recent Patents on Novel P2X7 Receptor Antagonists and their Potential for Reducing Central Nervous System Inflammation, Recent Patents on CNS Drug Discovery, 2010, pp. 35-45, vol. 5.
Furlan-Freguia, et al., P2X7 receptor signaling contributes to tissue factor-dependent thrombosis in mice, The Journal of Clinical Investigation, 2011, pp. 2932-2944, vol. 121 Issue 7.
Ghosh et al., "The monoacylglycerol lipase inhibitor JZL184 suppresses inflammatory pain in the mouse carrageenan model", Life Sci., Mar. 19, 2013, 498-505, vol. 92, No. 8-9.
Golub, et al., Molecular Classification of cancer: Class Discovery and class prediction by gene expression monitoring, Science, 1999, pp. 531-537, vol. 286.
Greene et al., "Protection for the Amino Group", Protective Groups in Organic Synthesis, Third Edition, John Wiley & Sons, 160 pages, 1999.
Grygorowicz, et al., Temporal expression of P2X7 purinergic receptor during the course of experimental autoimmune encephalomyelitis, Neurochemistry International, Sep. 9, 2010, pp. 823-829, vol. 57.
Guile, et al., Antagonists of the P2X7 Receptor. From Lead Identification to Drug Development, Journal of Medicinal Chemistry, May 28, 2009, pp. 3123-3141, vol. 52 Issue 10.
Guindon et al., "Peripheral antinociceptive effects of inhibitors of monoacylglycerol lipase in a rat model of inflammatory pain", Br J Pharmacol., 2011, 1464-1478, vol. 163.
Gunosewoyo, et al., P2X purinergic receptor ligands recently patented compounds, Expert Opin. Ther Patents, 2010, pp. 625-646, vol. 20 Issue 5.
Hackam, et al., "Translation of Research Evidence From animals to Humans", JAMA, vol. 296 (14): pp. 1731-1732 (2006).
Hajrasouliha et al., "Endogenous cannabinoids contribute to remote ischemic preconditioning via cannabinoid CB2 receptors in the rat heart", Eur J Pharmacol, 2008, 246-252, vol. 579.
Hauer et al., "Glucocorticoid-endocannabinoid interaction in cardiac surgical patients: relationship to early cognitive dysfunction and late depression", Rev Neurosci., 2012, 681-690, vol. 23, No. 5-6.
Herkenam et al., "Cannabinoid receptor localization in brain", Proc. Nat. Acad. Sci., 1990, 1932-1936, vol. 87, No. 5.
Hernandez-Torres et al., "A Reversible and Selective Inhibitor of Monoacylglycerol Lipase Ameliorates Multiple Sclerosis", Angew Chem Int Ed Engl., Dec. 8, 2014, 13765-13770, vol. 53, No. 50.
Hill et al., "Circulating endocannabinoids and N-acyl ethanolamines are differentially regulated in major depression and following exposure to social stress", Psychoneuroendocrinology, Sep. 3, 2009, 1257-1262, vol. 34, No. 8.
Hill et al., "Reductions in circulating endocannabinoid levels in individuals with post-traumatic stress disorder following exposure to the World Trade Center attacks", Psychoneuroendocrinology, 2013, 2952-2961, vol. 38, No. 12.
Hill et al., "Serum Endocannabinoid Content is Altered in Females with Depressive Disorders: A Preliminary Report", Pharmacopsychiatry, Mar. 2008, 48-53, vol. 41, No. 2.
Hudson, Derek, Methodological Implications of Simultaneous Solid-Phase peptide Synthesis, J.Org. Chem, 1988, pp. 617-624, vol. 53.
International Search Report and Written Opinion for International Application No. PCT/EP2021/057764 dated Jun. 8, 2021.
International Search Report and Written Opinion for International Application No. PCT/IB2019/058240 dated Jan. 10, 2020.
International Search Report and Written Opinion for International Application No. PCT/IB2019/058241 dated Jan. 10, 2020.
International Search Report and Written Opinion for International Application No. PCT/IB2020/059099 dated Nov. 24, 2020.

(56) References Cited

OTHER PUBLICATIONS

Ji, et al., P2X7 deficiency attenuates hypertension and renal injury in deoxycorticosterone acetate-salt hypertension, Am J Physiol Renal Physiol, 2012, pp. F1207-F1215, vol. 303.

Jordan, "Tamoxifen: a Most Unlikely Pioneering Medicine", Nature Reviews, vol. 2: pp. 205-213, (Mar. 2003).

Jung et al., "Uncoupling of the endocannabinoid signalling complex in a mouse model of fragile X syndrome", Nature Communications, 2012, 1080., vol. 3.

Katz et al., "Endocannabinoid Degradation Inhibition Improves Neurobehavioral Function, Blood-Brain Barrier Integrity, and Neuroinflammation following Mild Traumatic Brain Injury", J Neurotrauma, Mar. 1, 2015, 297-306, vol. 32, Issue 5.

Keating, et al., P2X7 Receptor-Dependent Intestinal Afferent Hypersensitivity in a Mouse Model of Postinfectious Irritable Bowel Syndrome, The Journal of Immunology, Jun. 22, 2011, pp. 1467-1474, vol. 187.

Keller, et al., "Radiosynthesis and Preclinical Evaluation of [18F]F-DPA, A Novel Pyrazolo[1,5a]pyrimidine Acetamide TSPO Radioligand, in Healthy Sprague Dawley Rats", Molecular Imaging and Biology, 2017, pp. 736-745, vol. 19.

Killeen, et al., Signaling through purinergic receptors for ATP induce human cutaneous innate and adaptive th17 responses:implications in the pathogenesis of psoriasis, The Journal of Immunology, 2013, pp. 4324-4336, vol. 190.

Kim, et al., Blockade of P2X receptor prevents astroglial death in the dentate gyrus following pilocarpine-induced status epilepticus, Neurological research, 2009, pp. 982-988, vol. 31.

Kinsey et al., "Blockade of Endocannabinoid-Degrading Enzymes Attenuates Neuropathic Pain", J Pharmacol Exp Ther., Sep. 2009, 902-910, vol. 330, No. 3.

Larsen, et al., "A text book of Drug Design and Development", Index; pp. 1-18 (1991).

Ligresti et al., "From endocannabinoid profiling to 'endocannabinoid therapeutics", Curr Opin Chem Biol., Jun. 2009, 321-331, vol. 13, No. 3.

Long et al., "Characterization of Monoacylglycerol Lipase Inhibition Reveals Differences in Central and Peripheral Endocannabinoid Metabolism", Chem Biol., Jul. 31, 2009, 744-753, vol. 16, No. 7.

Long et al., "Selective blockade of 2-arachidonoylglycerol hydrolysis produces cannabinoid behavioral effects", Nat Chem Biol., Jan. 2009, 37-44, vol. 5, No. 1.

Manske, R.H.F. and Kulka, M., "The Skraup Synthesis of Quinolines", Org. Reaction, 1953, 59-98, vol. 7.

Marcellino, et al., On the role of P2X7 receptors in dopamine nerve cell degeneration in a rat model of Parkinson's disease: studies with the P2X7 receptor antagonist A-438079, J Neural Transm, Apr. 13, 2010, pp. 681-687, vol. 117.

Martins, et al., The role of P2X7 purinergic receptors in inflammatory and nociceptive changes accompanying cyclophosphamide-induced haemorrhagic cystitis in mice, British Journal of Pharmacology, 2012, pp. 183-196, vol. 165.

Matsuda et al., "Structure of a cannabinoid recepter and functional expresion of the cloned cDNA", Nature, 1990, 561-564, vol. 346.

Mechoulam et al., "Identification of an endogenous 2-monoglyceride, present in canine gut, that binds to cannabinoid receptors", Biochem Pharmacol, 1995, 83-90, vol. 50.

Miller et al., "Controlled-deactivation cb1 receptor ligands as a novel strategy to lower intraocular pressure", Pharmaceuticals, 2018, 1-8, vol. 11, No. 50.

Muller, et al., Apotential role for P2X7r in allergic airway inflammation in mice and humans, American Journal of Respiratory Cell and molecular Biology, 2011, pp. 456-464, vol. 44.

Mulvihill et al., "Therapeutic potential of monoacylglycerol lipase inhibitors", Life Sci., Mar. 19, 2013, 492-497, vol. 92, No. 8-9.

Munro et al., "Molecular characterization of a peripheral receptor for cannabinoids", Nature, 1993, 61-65, vol. 365.

Nicholas Bodor, "Novel Approaches to the Design of Safer Drugs: Soft Drugs and Site-Specific Chemical Delivery Systems", Advances in Drug Research, 1984, pp. 255-331, vol. 13.

Nikitenko, A.A., et al., "Selective Hydrolysis of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate as a Key Step in the Large-Scale Synthesis of Bicyclic Heteroaryl Carboxyaldehydes", Org. Process Res. Dev., 2006, 712-716, vol. 10, No. 4.

Nithipatikom et al., "2-Arachidonoylglycerol: a novel inhibitor of androgen-independent prostate cancer cell invasion", Cancer Res., Dec. 15, 2004, 8826-8830, vol. 64, No. 24.

Nithipatikom et al., "A new class of inhibitors of 2-arachidonoylglycerol hydrolysis and invasion of prostate cancer cells", Biochem Biophys Res Commun., Jul. 15, 2005, 1028-1033, vol. 332, No. 4.

Nithipatikom et al., "Anti-proliferative effect of a putative endocannabinoid, 2-arachidonylglyceryl ether in prostate carcinoma cells", Prostaglandins Other Lipid Mediat., Feb. 9, 2011, 34-43, vol. 94, No. 1-2.

Nomura et al., "Endocannabinoid Hydrolysis Generates Brain Prostaglandins That Promote Neuroinflammation", Science, Nov. 11, 2011, 809-813, vol. 334, No. 6057.

Oyanguren-Desez, et al., Gain-of-function of P2X7 receptor gene variants in multiple sclerosis, Cell Calcium, Sep. 8, 2011, pp. 468-472, vol. 50.

Pacher et al., "Pleiotropic effects of the CB2 cannabinoid receptor activation on human monocyte migration: implications for atherosclerosis and inflammatory diseases", Amer J Physiol, 2008, H1133-H1134, vol. 294.

Parvathenani, et al., P2X7 Mediates Superoxide Production in Primary Microglia and Is Up-regulated in a Transgenic Mouse Model of Alzheimer's Disease, The Journal of Biological Chemistry, Jan. 27, 2003, pp. 13309-13317, vol. 278 Issue 15.

Pasquarelli et al., "Contrasting effects of selective MAGL and FAAH inhibition on dopamine depletion and GDNF expression in a chronic MPTP mouse model of Parkinson's disease", Neurochem Int., Nov. 2017, 14-24, vol. 110.

Pasquarelli et al., "Evaluation of monoacylglycerol lipase as a therapeutic target in a transgenic mouse model of ALS", Neuropharmacology, Sep. 15, 2017, 157-169, vol. 124.

Patel et al., "The endocannabinoid system as a target for novel anxiolytic drugs", Neurosci Biobehav Rev., May 2017, 56-66, vol. 76, Part A.

Paulekuhn, et al., "Trends in Active Pharmaceutical Ingredient Salt Selection based on Analysis of the Orange Book Database", Journal of Medicinal Chemistry, 2007, pp. 6665-6672, vol. 50 Issue 26.

Pike, Victor W., "Hypervalent aryliodine compounds as precursors for radiofluorination", J. Label Compd Radiopharm., 2018, pp. 196-227, vol. 61.

Piomelli, "The molecular logic of endocannabinoid signalling", Nat Rev Neurosci, 2003, 873-884, vol. 4.

Piro et al., "A Dysregulated Endocannabinoid-Eicosanoid Network Supports Pathogenesis in a Mouse Model of Alzheimer's Disease", Cell Rep., Jun. 28, 2012, 617-623, vol. 1, No. 6.

Ramesh et al., "Blockade of Endocannabinoid Hydrolytic Enzymes Attenuates Precipitated Opioid Withdrawal Symptoms in Mice", J Pharmacol Exp Ther., Oct. 2011, 173-185, vol. 339, No. 1.

Robinson, et al., "Discovery of the Hemifumarate and (r-L-Alanyloxy)methyl Ether as Prodrugs of an Antirheumatic Oxindole: Prodrugs for the Enolic OH Group"; Journal of Medicinal Chemistry, vol. 39 (1); pp. 10-18 (1996).

Romagnoli, et al., The P2X 7 receptor as a therapeutic target, Expert Opin. Ther., 2008, pp. 647-661, vol. 15 Issue 5.

Rudolph, et al., Novel methyl substituted 1-(5,6-dihydro-[1,2,4]triazolo[4,3-a]pyrazin-7(8H)-yl)methanones are P2X7 antagonists, Bioorganic & Medicinal Chemistry Letters, Jun. 9, 2015, pp. 3157-3163, vol. 25.

Sanz, et al., Activation of Microglia by Amyloid Requires P2X7 Receptor Expression1, The Journal of Immunology, 2009, pp. 4378-4385, vol. 182.

Schlosburg et al., "Chronic monoacylglycerol lipase blockade causes functional antagonism of the endocannabinoid system", Nat Neurosci., Sep. 13, 2010, 1113-1119, vol. 9.

Shan, et al., "Prodrug Strategies Based on Intramolecular Cyclization Reactions", Journal of Pharmaceutical Sciences, vol. 86 (7): pp. 765-767 (Jul. 1977).

(56) References Cited

OTHER PUBLICATIONS

Sharp, et al., P2x7 deficiency suppresses development of experimental autoimmune encephalomyelitis, Journal of Neuroinflammation, Aug. 8, 2008, pp. 1-13, vol. 5 Issue 33.
Simone, Part XIV - Oncology, Textbook of Medicine, 1996, 20th edition, pp. 1004-1010, vol. 1.
Skaper, et al., The P2X7 purinergic receptor: from physiology to neurological disorders, The FASEB Journal, 2010, pp. 337-345, vol. 24.
Solini, et al., Enhanced P2X7 Activity in Human Fibroblasts From Diabetic Patients A Possible Pathogenetic Mechanism for Vascular Damage in Diabetes, Arterioscler Thromb Vasc Biol., 2004, pp. 1240-1245, vol. 24.
Stahl et al., "Handbook of Pharmaceutical Salts", International Union of Pure and Applied Chemistry, Index, pp. 1-3, 2002.
Sticht et al., "Inhibition of monoacylglycerol lipase attenuates vomiting in Suncus murinus and 2-arachidonoyl glycerol attenuates nausea in rats", Br J Pharmacol., Apr. 2012, 2425-2435, vol. 165, No. 8.
Straiker et al., "Monoacylglycerol Lipase Limits the Duration of Endocannabinoid-Mediated Depolarization-Induced Suppression of Excitation in Autaptic Hippocampal Neurons", Mol Pharmacol., 2009, pp. 1220-1227, vol. 76, No. 6.
Sugiura et al., "2-Arachidonoylgylcerol: A Possible Endogenous Cannabinoid Receptor Ligand in Brain", Biochem Biophys Res Commun, 1995, 89-97, vol. 215.
Sugiura et al., "Biosynthesis and degradation of anandamide and 2-arachidonoyiglycerol and their possible physiological significance", Prostaglandins Leukot Essent Fatty Acid, Feb.-Mar. 2002, 173-192, vol. 66, No. 2-3.
Suguira et al., "Biochemistry, pharmacology and physiology of 2-arachidonoylglycerol, an endogenous cannabinoid receptor ligand", Prog Lipid Res, 2006, 405-446, vol. 45, No. 5.
Surprenant, et al., Signaling at Purinergic P2X Receptors, Annu. Rev. Physiol, Oct. 13, 2008, pp. 333-359, vol. 71.
Terrone et al., "Inhibition of monoacylglycerol lipase terminates diazepam-resistant status epilepticus in mice and its effects are potentiated by a ketogenic diet", Epilepsia, Jan. 2018, 79-91, vol. 59, No. 1.
Thiboutot, et al., Inflammasome Activation by propionibacterium acnes: the Story of IL-1 in Acne continues to unfold, Journal Of Investigative Dermatology, 2014, pp. 595-597, vol. 134.
Tuo et al., "Therapeutic Potential of Fatty Acid Amide Hydrolase, Monoacylglycerol Lipase, and N-Acylethanolamine Acid Amidase Inhibitors", J Med Chem., Jan. 12, 2017, 4-46, vol. 60, No. 1.
Vergani, et al., Effects of the purinergic Inhibitor Oxidized ATP in a model of Islet Allograft rejection, Diabetes, 2013, pp. 1665-1675, vol. 62.
Vergani, et al., Long term Heart Transplant Survival by targeting the Ionotropic Purinergic receptor P2X7, Circulation, 2013, pp. 463-475, vol. 127.
Von Ruden et al., "Inhibition of monoacylglycerol lipase mediates a cannabinoid 1-receptor dependent delay of kindling progression in mice", Neurobiol Dis., May 2015, 238-245, vol. 77.
Walter et al., "ATP Induces a Rapid and Pronounced Increase in 2-Arachidonoyiglycerol Production by Astrocytes, a Response Limited by Monoacylglycerol Lipase", J Neurosci., Sep. 15, 2004, 8068-8074, vol. 24, No. 37.
Wang et al., "Treating a novel plasticity defect rescues episodic memory in Fragile X model mice", Mol Psychiatry, 2018, 1798-1806, vol. 23, No. 8.
Wenzel et al., "Novel multi-target directed ligand-based strategies for reducing neuroinflammation in Alzheimer's disease", Life Sci., Aug. 15, 2018, 314-322, vol. 207.
Wilkerson et al., "The Selective Monoacylglycerol Lipase Inhibitor MJN110 Produces Opioid-Sparing Effects in a Mouse Neuropathic Pain Model", J Pharmacol Exp Ther., Apr. 2016, 145-156, vol. 357, No. 1.
Wilson et al., "A high-throughput-compatible assay for determining the activity of fatty acid amide hydrolase", Anal Biochem., Jul. 15, 2003, 270-275, vol. 318, No. 2.
Yi et al., "Reductions in circulating endocannabinoid 2-arachidonoylglycerol levels in healthy human subjects exposed to chronic stressors", Progress in Neuro-Psychopharmacology and Biological Psychiatry, 2016, 92-97, vol. 67, No. 3.
Zhang et al., "Inhibition of monoacylglycerol lipase prevents chronic traumatic encephalopathy-like neuropathology in a mouse model of repetitive mild closed head injury", J Cereb Blood Flow Metab., Mar. 31, 2015, 706, vol. 35, Issue No. 4.
Boger, Dale L,"The Difference a Single Atom Can Make: Synthesis and Design at the Chemistry-Biology Interface" The Journal of Organic Chemistry, vol. 82, No. 23, pp. 11961-11980, Sep. 25, 2017.
Catherine, Goodman, "One-atom activity", Nature Chemical Biology, vol. 7, 654 Pages, Aug. 28, 2011.
Hu et al., "Activity cliffs produced by single-atom modification of active compounds: Systematic identification and rationalization based on X-ray structures", European Journal of Medicinal Chemistry, vol. 207, No. 112846, pp. 1-10, Sep. 16, 2020.
International Search Report and Written Opinion, received for PCT Application No. PCT/US2009/041249, mailed on Jul. 31, 2009, 7 pages.
International Search Report and Written Opinion, received for PCT Application No. PCT/US2014/027450, mailed on Aug. 12, 2014, 17 pages.
International Search Report and Written Opinion, received for PCT Application No. PCT/US2014/027505, mailed on Jul. 1, 2014, 16 pages.
International Search Report and Written Opinion, received for PCT Application No. PCT/US2014/027540, mailed on Jun. 17, 2014, 13 pages.
International Search Report and Written Opinion, received for PCT Application No. PCT/US2015/046710, mailed on Oct. 15, 2015, 6 pages.
International Search Report and Written Opinion, received for PCT Application No. PCT/US2015/046852, mailed on Oct. 15, 2015, 6 pages.
International Search Report and Written Opinion, received for PCT Application No. PCT/US2014/027522, mailed on Jul. 1, 2014, 8 pages.
Lerner, Louise, "Speeding Up Molecule Design With a New Technique That Can Delete Single Atoms", SciTechDaily, 9 Pages, Mar. 22, 2024.
Maulide, Nuno, "When changing one atom makes molecules better" Medical University of Vienna, 4 Pages, Mar. 4, 2019.
Swanson et al., "Identification of (R)-(2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone (JNJ 54166060), a Small Molecule Antagonist of the P2X7 receptor", Journal of Medicinal Chemistry, vol. 59, No. 18, pp. 8535-8548, Sep. 22, 2016.

RADIOLABELLED MGL PET LIGANDS

CROSS-REFERENCE TO RELATED APPLICATIONS

This application is a continuation of U.S. patent application Ser. No. 17/036,919, filed on Sep. 29, 2020, now U.S. Pat. No. 11,839,663, which claims priority to U.S. patent application Ser. No. 62/907,852, filed on Sep. 30, 2019, each of which is incorporated herein in its entirety.

FIELD OF THE INVENTION

The present invention relates to a novel, selective, compound having monoacylglycerol lipase (MGL) affinity, and in one embodiment containing a positron-emitting radioligand to enable positron-emission tomography (PET); a pharmaceutical composition comprising the compound, using the compound to assess MGL receptor expression, distribution and enzyme occupancy, and diagnosis of diseases, disorders or conditions associated with MGL receptor activity in subjects, in particular humans.

BACKGROUND OF THE INVENTION

Cannabis Sativa and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda et al., *Nature*, 1990, 346, 561-4) and cannabinoid receptor type 2 (CB2) (Munro et al., *Nature*, 1993, 365, 61-5). CB1 receptor is one of the most abundant G-protein coupled receptor expressed in the brain (Herkenam et al., *Proc. Nat. Acad. Sci.*, 1990, 87 (5), 1932-1936). CB1 is also expressed peripherally in the liver, gastrointestinal tract, pancreas, adipose tissue and skeletal muscles (Di Marzo et al., *Curr Opin Lipidol*, 2007, 18, 129-140). CB2 is predominantly expressed in immune cells such as monocytes (Pacher et al., *Amer J Physiol*, 2008, 294, H1133-H1134) and under certain conditions (inflammation) in the brain ((Benito et al., *Brit J Pharmacol*, 2008, 153, 277-285) and in skeletal (Cavuoto et al., *Biochem Biophys Res Commun*, 2007, 364, 105-110) and cardiac muscles (Hajrasouliha et al., *Eur J Pharmacol*, 2008, 579, 246-252).

In 1992, N-arachidonoylethanolamine (AEA or anandamide) was found to be an endogenous ligand for cannabinoid receptors (Devane et al., *Science*, 1992, 258, 1946-9). Subsequently, 2-arachidonoylglycerol (2-AG) was also identified as an additional endogenous ligand for the cannabinoid receptors (Mechoulam et al., *Biochem Pharmacol*, 1995, 50, 83-90; Sugiura et al., *Biochem Biophys Res Commun*, 1995, 215, 89-97). Concentrations of 2-AG were reported to be at least 100 times higher than these of anandamide in the rat brain (Buczynski and Parsons, *Brit J Pharmacol*, 2010, 160 (3), 423-42). Therefore 2-AG may play more essential physiological roles than anandamide in the brain endocannabinoid system (Sugiura et al. *Prostaglandins Leukot Essent Fatty Acids.*, 2002, February-March, 66(2-3):173-92). The endocannabinoid 2-AG is a full agonist for CB1 and CB2 receptors, while anandamide is a partial agonist for both receptors (Suguira et al., *Prog Lipid Res*, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., *Chem Rev.* 2008, 108(5):1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., *Biochem Pharmacol*, 1995, 50, 83-90; Sugiura et al., *Biochem Biophys Res Commun*, 1995, 215, 89-97; Long et al., *Nat Chem Biol.* 2009 January;5(1):37-44;), Schlosburg et al, *Nat Neurosci.*, 2010, September;13(9):1113-9) and peripheral tissues (Long et al., *Chem Biol.*, 2009 Jul. 31;16 (7):744-53). Anandamide is hydrolyzed by fatty acid amide hydrolase (FAAH) (Piomelli, *Nat Rev Neurosci*, 2003, 4, 873-884). MGL exists in both soluble and membrane bound forms (Dinh et al., *Proc Natl Acad Sci U S A.*, 2002, Aug. 6;99(16):10819-24). In the brain MGL is located in presynaptic neurons (Straiker et al., *Mol Pharmacol.*, 2009, December;76(6):1220-7) and astrocytes (Walter et al., *J Neurosci.*, 2004, Sep. 15;24(37):8068-74) within regions associated with high CB1 receptor density. Compared to wild-type controls, genetic ablation of MGL expression produces 10-fold increase in brain 2-AG levels without affecting anandamide concentration (Schlosburg et al., *Nat Neurosci.*, 2010, September;13(9):1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., *Nat Chem Biol.*, 2009, January, 5(1):37-44; Ghosh et al., *Life Sci.*, 2013, Mar. 19, 92(8-9):498-505; Bedse et al., *Biol Psychiatry.*, 2017, Oct. 1, 82(7):488-499; Bernal-Chico et al., *Glia.*, 2015, January, 63(1):163-76; Patel et al. *Neurosci Biobehav Rev.*, 2017, May, 76(Pt A):56-66; Betse et al., *Transl Psychiatry.*, 2018, Apr. 26, 8(1):92). In addition to the role of MGL in terminating 2-AG signaling, MGL modulation, including MGL inhibition also promotes CB1/2-independent effects on neuroinflammation (Nomura et al., *Science.*, 2011, Nov. 11;334(6057):809-13). MGL modulation, including MGL inhibition leads to reduction in proinflammatory prostanoid signaling in animal models of traumatic brain injury (Katz et al., *J Neurotrauma.*, 2015, Mar. 1;32 (5):297-306; Zhang et al., *J Cereb Blood Flow Metab.*, 2015, Mar. 31;35(4):706), neurodegeneration including Alzheimer's disease (Piro et al., Cell Rep., 2012, Jun. 28, 1(6):617-23; Wenzel et al., Life Sci., 2018, Aug. 15, 207:314-322; Chen et al., Cell Rep., 2012, Nov. 29, 2(5):1329-39), Parkinson's disease (Nomura et al., Science, 2011, Nov. 11, 334(6057), 809-13; Pasquarelli et al., Neurochem Int., 2017, November, 110:14-24), amyotrophic lateral sclerosis (Pasquarelli et al., Neuropharmacology, 2017, Sep. 15, 124: 157-169), multiple sclerosis (Hernadez-Torres et al., Angew Chem Int Ed Engl., 2014, Dec. 8, 53(50):13765-70; Bernal-Chico et al., Glia., 2015, January, 63(1):163-76), Huntington's disease (Covey et al., Neuropsychopharmacology, 2018, 43, 2056-2063), Tourette syndrome and status epilepticus (Terrone et al., *Epilepsia.*, 2018, Jan., 59(1), 79-91; von Ruden et al., *Neurobiol Dis.*, 2015, May;77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J Med Chem.*, 2017, Jan. 12, 60(1), 4-46; Mulvihill et al., *Life Sci.*, 2013, Mar. 19, 92(8-9), 492-7).

Endocannabinoid hypoactivity is a risk factor for the treatment of depression, anxiety and post-traumatic stress disorders. Millennia of human use of cannabis sativa, and a brief period in which humans were treated with the endocannabinoid antagonist, rimonabant, provide support for that hypothesis. 2-AG levels are decreased in individuals with major depression (Hill et al., *Pharmacopsychiatry.*, 2008, March; 41(2): 48-53; Hill et al., *Psychoneuroendocrinology.*, 2009, September; 34(8): 1257-1262.). Low circulating 2-AG levels predict rates of depression (Hauer et al., *Rev Neurosci.*, 2012, 23(5-6):681-90). Reduced circulating 2-AG has been found in patient with post-traumatic stress disorder (PTSD) (Hill et al., *Psychoneuroendocrinology*, 2013, 38 (12), 2952-2961). Healthy volunteers exposed to chronic stressors exhibited progressively diminished circulating 2-AG levels which correlated with the onset of reductions in measures of positive emotions (Yi et al., *Progress in Neuro-Psychopharmacology and Biological Psychiatry*, 2016, 67 (3), 92-97). The CB1 receptor inverse agonist/antagonist Rimonabant has been withdrawn from the market due to the high incidence of severe depression and suicidal ideation (Christensen et al., *The Lancet*, 2007, 370, 1706-1713). Therefore, MGL modulators are potentially useful for the treatment of mood disorders, anxiety and PTSD.

Cannabinoid receptor agonists are clinically used to treat pain, spasticity, emesis and anorexia (Di Marzo, et al., *Annu Rev Med.*, 2006, 57:553-74; Ligresti et al., *Curr Opin Chem Biol.*, 2009, June;13(3):321-31). Therefore, MGL modulators, including MGL inhibitors are also potentially useful for these indications. MGL exerts CB1-dependant antinociceptive effects in animal models of noxious chemical, inflammatory, thermal and neuropathic pain (Guindon et al., *Br J Pharmacol.*, 2011, August;163(7):1464-78; Kinsey et al., *J Pharmacol Exp Ther.*, 2009, September;330(3):902-10; Long et al., *Nat Chem Biol.*, 2009, January;5(1):37-44). MGL blockade reduces mechanical and acetone induced cold allodynia in mice subjected to chronic constriction injury of the sciatic nerve (Kinsey et al., *J Pharmacol Exp Ther.*, 2009, September;330(3):902-10). MGL inhibition produces opiate-sparing events with diminished tolerance, constipation, and cannabimimetic side effects (Wilkerson et al., *J Pharmacol Exp Ther.*, 2016, April;357(1):145-56). MGL blockade is protective in model of inflammatory bowel disease (Alhouayek et al., *FASEB J.*, 2011, August;25(8): 2711-21). MGL inhibition also reverse Paclitaxel-induced nociceptive behavior and proinflammatory markers in a mouse model of chemotherapy-induced neuropathy (Curry et al., *J Pharmacol Exp Ther.*, 2018, July;366(1):169-18).

Inhibition of 2-AG hydrolysis exerts anti-proliferative activity and reduction in prostate cancer cell invasiveness (Nithipatikom et al., *Cancer Res.*, 2004, Dec. 15, 64(24): 8826-30; Nithipatikom et al., *Biochem Biophys Res Commun.*, 2005, Jul. 15,332(4):1028-33; Nithipatikom et al., *Prostaglandins Other Lipid Mediat*, 2011, February, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br J Pharmacol.*, 2012, April, 165(8):2425-35).

MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J Pharmacol Exp Ther.*, 2011, October, 339(1):173-85).

MGL modulators are also potentially useful for the treatment of eye conditions, including but not limited to, glaucoma and disease states arising from elevated intraocular pressure (Miller et al., *Pharmaceuticals*, 2018, 11, 50).

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides such as, for example, $^{15}O$, $^{13}N$, $^{11}C$ and $^{18}F$ for detection. There is a need to provide positron emission tomography radiotracers for evaluation of MGL's expression, distribution and occupancy by its inhibitors. The imaging agent would play a critical role in such a research and in the development of therapeutic candidates targeting MGL.

SUMMARY OF THE INVENTION

The present invention relates to a compound having the Formula (I)

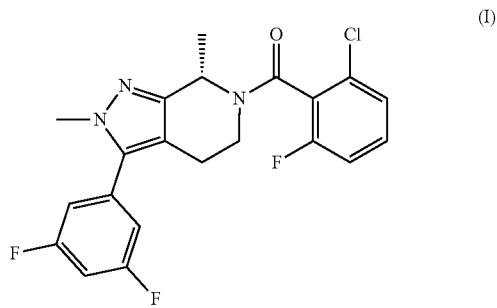 [SMILES: C[C@H]1c2nn(C)c(-c3cc(F)cc(F)c3)c2CCN1C(=O)c1c(F)cccc1Cl]

(I)

or a pharmaceutically acceptable salt, or a solvate thereof. In one embodiment, the compound of Formula (I) has at least one atom that is radioactive.

In a particular embodiment, the compound of Formula (I) is a compound of Formula (IA),

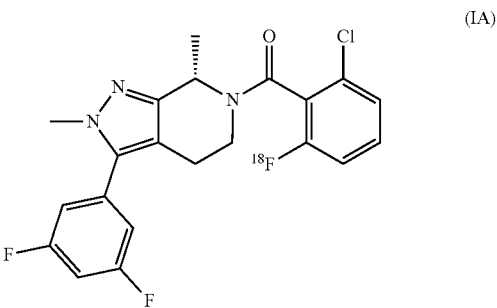 [SMILES: C[C@H]1c2nn(C)c(-c3cc(F)cc(F)c3)c2CCN1C(=O)c1c([18F])cccc1Cl]

(IA)

or a pharmaceutically acceptable salt or a solvate thereof.

The invention also relates to a pharmaceutical composition comprising a compound of Formula (I) (as well as a compound of Formula (IA)) or a pharmaceutically acceptable salt thereof and a pharmaceutically acceptable carrier or diluent. In a particular embodiment, said pharmaceutical composition is particularly suitable for diagnosis and may be referred to therefore as a diagnostic pharmaceutical composition. In particular, said pharmaceutical composition is a sterile solution. Thus, illustrative of the invention is a sterile solution comprising a compound of Formula (I) (as well as a compound of Formula (IA)) described herein.

The invention further relates to the use of a compound of Formula (I) (as well as a compound of Formula (IA)) as an imaging agent. Therefore, exemplifying the invention is a use of a compound of Formula (I) (as well as a compound of Formula (IA)) as described herein, for, or a method of, imaging a tissue, cells or a mammal, in vitro or in vivo. In particular, the invention relates to a compound of Formula (I) (as well as a compound of Formula (IA)) as described herein, for use as a contrast agent for imaging a tissue, cells or a mammal, in vitro, ex vivo, or in vivo. The invention further relates to a composition comprising a compound of Formula (I) (as well as a compound of Formula (IA)) for use as a contrast agent for imaging a tissue, cells or a mammal, in vitro, ex vivo, or in vivo.

The invention also relates to a method for imaging a tissue, cells or a mammal, comprising contacting with or providing or administering a detectable amount of a labelled compound of Formula (I) (as well as a compound of Formula (IA)) as described herein to a tissue, cells or a mammal, and detecting the compound of Formula (I) (as well as a compound of Formula (IA)).

Further exemplifying the invention is a method of imaging a tissue, cells or a mammal, comprising contacting with or providing or administering to a tissue, cells or a mammal, a compound of Formula (I) (as well as a compound of Formula (IA)) as described herein, and imaging the tissue, cells or mammal with a positron-emission tomography imaging system.

DETAILED DESCRIPTION OF THE INVENTION

Figure 1:
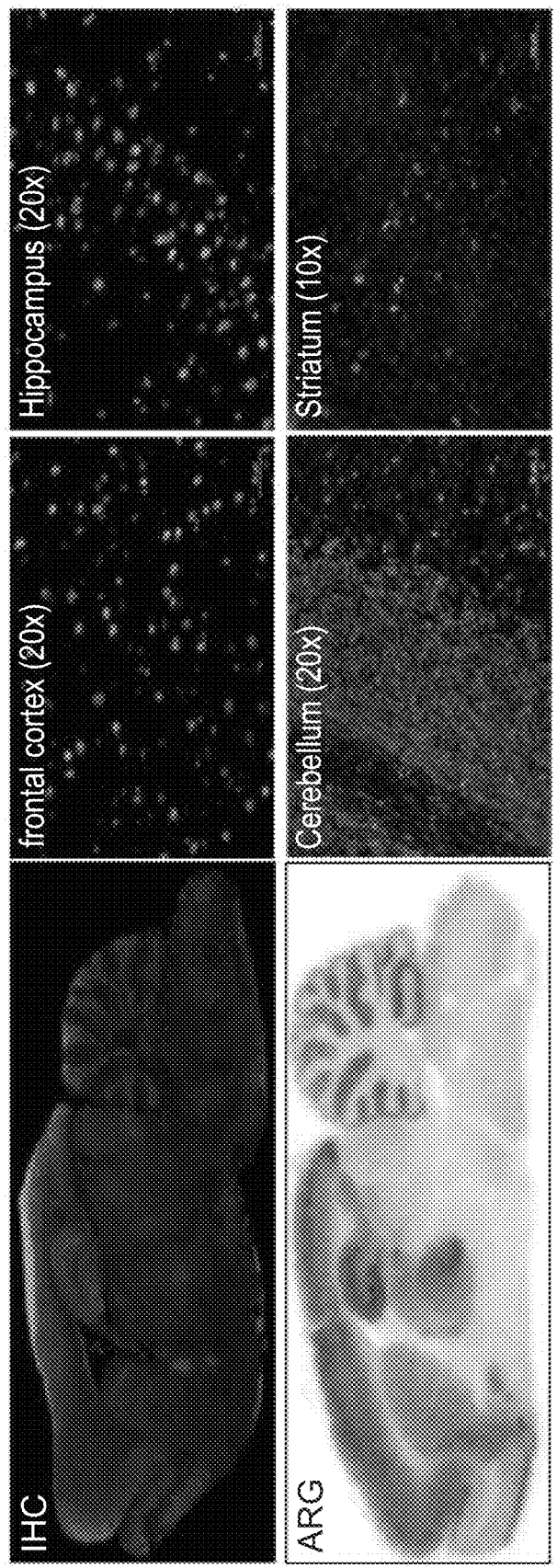
FIG. 1. Immunohistochemistry (IHC) staining of MGL on normal rat brain sections (sagittal view)

The present invention is directed to compounds of Formula (I) (as well as a compound of Formula (IA)) as defined herein before, and pharmaceutically acceptable salts thereof. The present invention is also directed to the precursor compound of Formula (IB), used in the synthesis of compounds of Formula (IA).

In one embodiment of the present invention, is a compound of Formula (I):

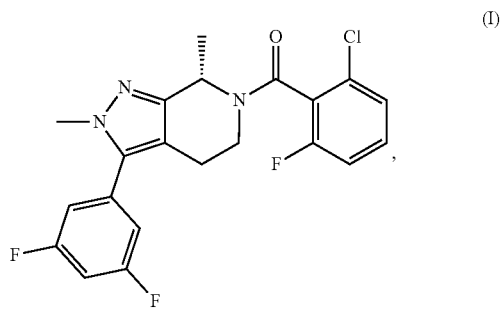 [SMILES: C[C@H]1c2nn(C)c(-c3cc(F)cc(F)c3)c2CCN1C(=O)c1c(F)cccc1Cl]

or a pharmaceutically acceptable salt, isotope, or a solvate thereof.

In one embodiment of the present invention, is a compound of Formula (IA):

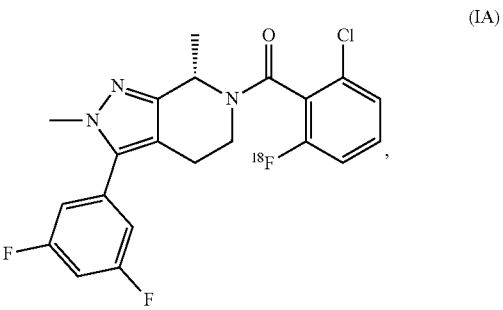 [SMILES: C[C@H]1c2nn(C)c(-c3cc(F)cc(F)c3)c2CCN1C(=O)c1c([18F])cccc1Cl]

or a pharmaceutically acceptable salt, or a solvate thereof.

In a further embodiment, the compound of Formula (I) as previously described is selected from the group consisting of:
(S)-(2-chloro-6-fluorophenyl)(3-(3,5-difluorophenyl)-2,7-dimethyl-2,4,5,7-tetrahydro-6H-pyrazolo[3,4-c]pyridin-6-yl)methanone; and
(S)-(2-chloro-6-($^{18}$F)fluorophenyl)(3-(3,5-difluorophenyl)-2,7-dimethyl-2,4,5,7-tetrahydro-6H-pyrazolo[3,4-c]pyridin-6-yl)methanone;
and pharmaceutically acceptable salts thereof.

As already mentioned, the compounds of Formula (I) (as well as a compound of Formula (IA)) and compositions comprising the compounds of Formula (I) (as well as a compound of Formula (IA)) can be used for imaging a tissue, cells or a host, in vitro or in vivo. In particular, the invention relates to a method of imaging or quantifying MGL's expression, distribution and occupancy by its inhibitors in tissue, cells or a host in vitro or in vivo. The cells and tissues are preferably central nervous system cells and tissues in which the MGL enzyme are abundant.

When the method is performed in vivo, the host is a mammal. In such particular cases, the compound of Formula (IA) is administered intravenously, for example, by injection with a syringe or by means of a peripheral intravenous line, such as a short catheter.

When the host is a human, the compound of Formula (IA) or a sterile solution comprising a compound of Formula (IA), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (IA), as defined herein, or a composition comprising a compound of Formula (IA) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (IA), as defined herein, or a sterile formulation comprising a compound of Formula (IA) to the human, and imaging the tissue or cells with a positron-emission tomography imaging system.

In a further embodiment, the invention relates to a method of imaging or quantifying MGL's expression in a mammal, comprising the intravenous administration of a compound of Formula (IA), or a composition comprising a compound of Formula (IA) to the mammal, and imaging with a positron-emission tomography imaging system.

In another embodiment, the invention relates to the use of a compound of Formula (IA) for imaging a tissue, cells or a host, in vitro or in vivo, or the invention relates to a compound of Formula (IA), for use in imaging a tissue, cells or a host in vitro or in vivo, using positron-emission tomography.

Definitions

As used herein, the term "composition" is intended to encompass a product comprising the specified ingredients in the specified amounts, as well as any product which results, directly or indirectly, from combinations of the specified ingredients in the specified amounts.

Addition salts of the compounds according to Formula (I) and of the compounds of Formula (IA) can also form stereoisomeric forms and are also intended to be encompassed within the scope of this invention.

The term "an MGL inhibitor containing a positron emission tomography ("PET") tracer radionuclide" means that one or more atoms of the MGL inhibitor are replaced PET tracer radionuclide. In some embodiments, a fluorine atom of the MGL inhibitor is replaced by $^{18}$F. In some embodiments, a carbon atom of the MGL inhibitor is replaced by $^{11}$C. In some embodiments a nitrogen atom of the MGL inhibitor is replaced by $^{13}$N. In some embodiments a nitrogen atom of the MGL inhibitor is replaced by $^{15}$O.

A "pharmaceutically acceptable salt" is intended to mean a salt of an acid or base of a compound represented by Formula (I) (as well as Formula (IA)) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use,* Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) (as well as Formula (IA)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) (as well as Formula (IA)) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) (as well as Formula (IA)) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methylglucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as MGL-modulators in the methods of the invention. Such methods for modulating MGL comprise the use of a therapeutically effective amount of at least one chemical compound of the invention.

In addition, some of the compounds of the present invention may form solvates with water (i.e., hydrates) or common organic solvents, and such solvates are also intended to be encompassed within the scope of this invention.

The term "host" refers to a mammal, in particular to humans, mice, dogs and rats.

The term "cell" refers to a cell expressing or incorporating the MGL enzyme.

The term "tissue" refers to a tissue expressing or incorporating the MGL enzyme.

Any formula given herein is also intended to represent unlabelled forms as well as isotopically labelled forms of the compounds. Isotopically labelled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2H$ (or chemical symbol D), $^3H$ (or chemical symbol T), $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labelled compound may be particularly preferred for PET or SPECT studies. Further, substitution with heavier isotopes such as deuterium (i.e., $^2H$, or D) may afford certain therapeutic advantages resulting from greater metabolic stability, for example increased in vivo half-life or reduced dosage requirements. Isotopically labelled compounds of this invention can generally be prepared by carrying out the procedures disclosed in the schemes or in the examples and preparations described below by substituting a readily available isotopically labelled reagent for a non-isotopically labelled reagent.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006).

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 1

| Term | Acronym |
| --- | --- |
| Aqueous | aq |
| Atmosphere | atm |
| Broad | br |
| Dimethylsulfoxide | DMSO |

TABLE 1-continued

| Term | Acronym |
| --- | --- |
| Diethyl ether | Ether, $Et_2O$ |
| Ethyl Acetate | EtOAc, or EA |
| Ethanol | EtOH |
| Electrospray ionization | ESI |
| Normal-phase silica gel chromatography | FCC |
| Grams | g |
| Hours | H, hr, hrs |
| High-pressure liquid chromatography | HPLC |
| Hertz | Hz |
| Liquid chromatography and mass spectrometry | LCMS |
| Molar | M |
| Mass to charge ratio | m/z |
| Methanol | MeOH |
| Milligrams | mg |
| Minute | min |
| Milliliter | mL |
| Microliter | μL |
| Millimoles | mmol |
| Mass spectrometry | MS |
| Normal | N |
| Nuclear magnetic resonance | NMR |
| $CF_3SO_3$— or triflate | OTf |
| Parts per million | ppm |
| Precipitate | ppt |
| Polytetrafluoroethylene | PTFE |
| Retention time | $R_t$ |
| Room temperature | rt |
| Saturated | sat |
| Supercritical Fluid Chromatography | SFC |
| Temperature | T |
| Thin layer chromatography | TLC |
| Volume in milliliters of solvent per gram of substrate | V, or volumes |

Preparative Examples

Exemplary compounds useful in methods of the invention will now be described by reference to the illustrative synthetic schemes for their general preparation below and the specific examples to follow.

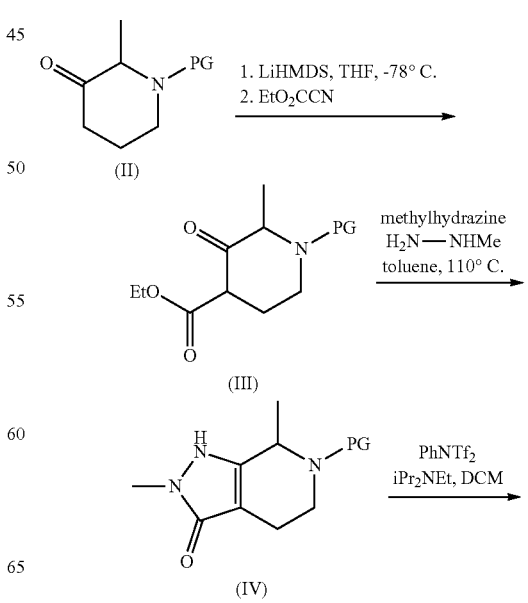

SCHEME 1

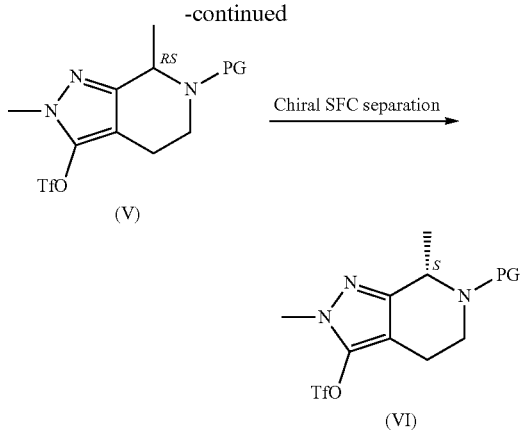

According to SCHEME 1, a keto-ester compound of formula (III), where PG is a suitable protecting group such as BOC (tert-butyloxycarbonyl is prepared from a commercially available or synthetically accessible compound of formula (II). For example, a compound of formula (II), where PG is BOC, is converted to compound (III), by treatment with a strong base such as lithium bis(trimethylsilyl)amide (LHMDS), in a suitable solvent such as tetrahydrofuran (THF), and the like, at a temperature of about −78° C. for 30 minutes, followed by treatment with ethyl cyanoformate at −78° C., for 2 a period of about 2 hours.

A compound of formula (III) is reacted with commercially available or synthetically accessible methylhydrazine, in a suitable solvent such as toluene, at a temperature of about 110° C., to provide a pyrazolone compound of formula (IV). Derivation of pyrazolone compound of formula (IV), with a sulfonate-based leaving group such as trifluoromethanesulfonyl (triflate), is achieved by is by reaction with a triflating agent such as trifluoromethanesulfonic anhydride ($Tf_2O$), a base such as triethylamine (TEA), pyridine, N-ethyldiisopropylamine (DIEA, DIPEA), and the like, in a suitable solvent such as DCM and the like. Milder triflating agents such as N-Phenylbis(trifluoromethanesufonimide) ($TF_2NPh$), a base such as TEA, DIEA, and the like, in a suitable solvent such as DCM, and the like; are used for better selectivity, to provide a compound of formula (V). Chiral separation of the mixture of compounds of formula (V), employing methods known to one skilled in the art provides a compound of formula (VI).

SCHEME 2

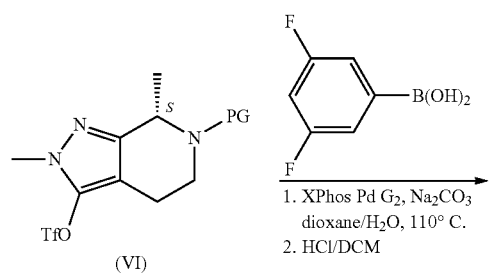

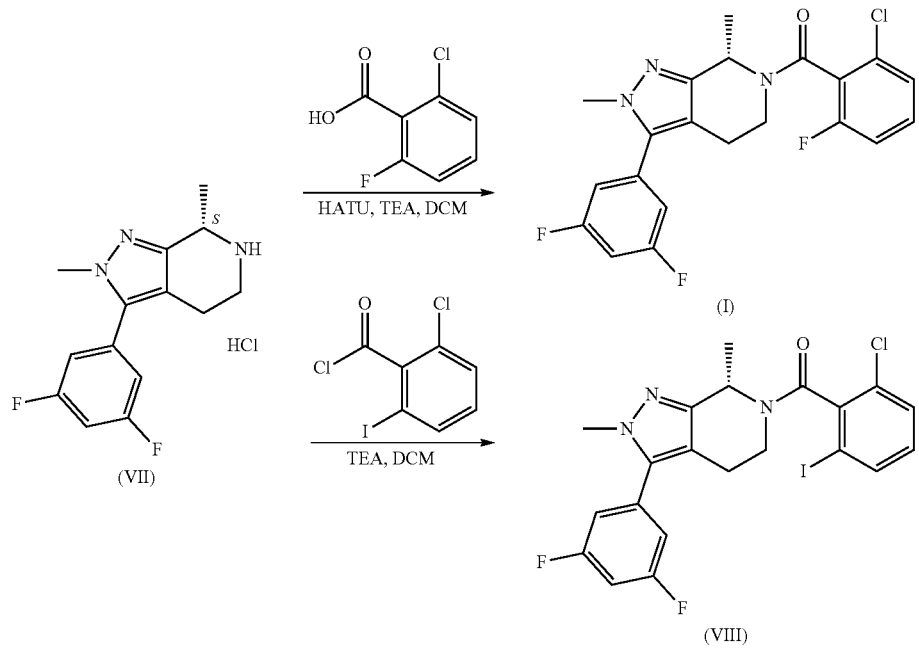

According to SCHEME 2, a compound of formula (VI), is coupled in a metal mediated cross coupling reaction with boronic acid such as (3,5-difluorophenyl)boronic acid, in the presence of a palladium catalyst such as [1,1'-bis(di-tert-butylphosphino)ferrocene]dichloropalladium(II) (PdCl₂ (dtbpf)), tetrakis(triphenylphosphine)palladium(0) (Pd (PPh₃)₄), [1,1'-bis(diphenylphosphino)ferrocene] dichloropalladium(II) (PdCl₂(dppf)), palladium(II)bis (triphenylphosphine) dichloride (Pd(PPh₃)₂Cl₂), XPhos-Pd-G2 precatalyst (chloro(2-dicyclohexylphosphino-2',4',6'-triisopropyl-1,1'-biphenyl)[2-(2'-amino-1,1'-biphenyl)] palladium(II)), and the like, a base such as K₃PO₄, aq. Na₂CO₃, Na₂CO₃, Cs₂CO₃, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h.

Cleavage of the BOC protecting group is achieved according to procedures known to one skilled in the art and employing established methodologies, such as those described in T. W. Greene and P. G. M. Wuts, "Protective Groups in Organic Synthesis," 3 ed., John Wiley & Sons, 1999. For example, under acidic conditions such as TFA/CH₂Cl₂, HCl/Dioxane, and the like, provides a compound of formula (VII).

A compound of Formula (I); is prepared by conventional amide bond forming techniques such as coupling reactions which are well known to those skilled in the art (such as HATU (1-[bis(dimethylamino)methylene]-1H-1,2,3-triazolo[4,5-b]pyridinium 3-oxid hexafluorophosphate), BOP (benzotriazol-1-yloxy-tris(dimethylamino)phosphonium hexafluorophosphate), or conversion of the acid to an acid chloride). For example, reaction of a compound of formula (VII) with commercially available or synthetically accessible 2-chloro-6-fluorobenzoic acid, where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris(dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt, to provide compound a of Formula (I).

2-Chloro-6-iodobenzoic acid is converted to 2-chloro-6-iodobenzoyl chloride by reaction with oxalyl chloride, in a suitable solvent such as DMC and the like, and a catalytic amount of dimethylformamide (DMF). A compound of formula (VIII); is prepared by conventional amide bond forming techniques such as a coupling reaction with 2-chloro-6-iodobenzoyl chloride; a suitable base such as triethylamine (TEA); in a suitable solvent such as dichloromethane (DCM), and the like; at room temperature; for a period of 12-24 h.

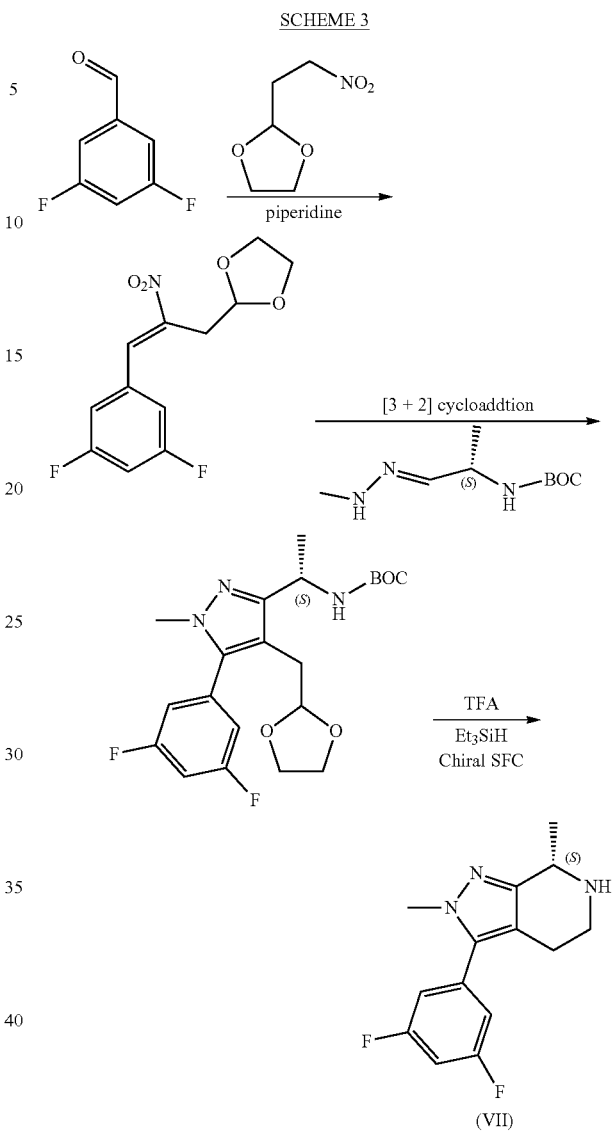

According to SCHEME 23, tert-butyl (S)-(1-oxopropan-2-yl)carbamate and methylhydrazine is condensed in a suitable solvent such as THF to afford tert-butyl (S,E)-(1-(2-methylhydrazineylidene)propan-2-yl)carbamate. 3,5-Difluorobenzaldehyde is treated with 2-(2-nitroethyl)-1,3-dioxolane in the presence of a catalytic amount of suitable base such as piperidine; in a suitable solvent such as toluene; at a temperature of 110° C. to provide (E)-2-(3-(3,5-difluorophenyl)-2-nitroallyl)-1,3-dioxolane.

(S)—N-(1-(4-((1,3-Dioxolan-2-yl)methyl)-5-(3,5-difluorophenyl)-1-methyl-1H-pyrazol-3-yl)ethyl)-1-(11-methyl)-1-(11-oxidaneyl)boranamine is prepared through [3+2] cycloaddition of tert-butyl (S,E)-(1-(2-methylhydrazineylidene) propan-2-yl)carbamate and (E)-2-(3-(3,5-difluorophenyl)-2-nitroallyl)-1,3-dioxolane at a temperature of 40° C. Subsequent global deprotection and cyclization by treatment with trifluoroacetic acid and triethylsilane at 55° C. affords a compound of formula (VII). In cases where a racemic mixture is obtained, a single enantiomer by chiral SFC purification may be employed.

SCHEME 4

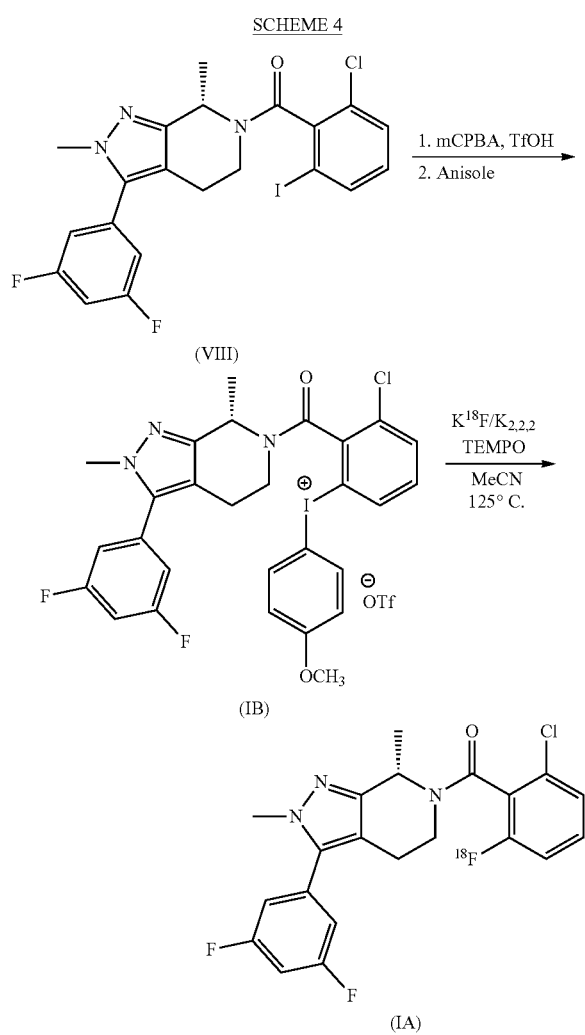

According to SCHEME 4, an iodoarene compound of formula (VIII) is oxidized with chloroperoxybenzoic acid (m-CPBA) in the presence of a Brønsted acid such as tosylic acid or trifluorosulfonic acid, preferably trifluorosulfonic acid; and electron-rich anisole as the directing group; in a suitable solvent such as DCM, and the like; to provide the diaryliodonium salt compound of Formula (IB).

The labelling reaction is carried out in a solvent such as acetonitrile ($CH_3CN$), water ($H_2O$), N,N-dimethylformamide (DMF), or dimethyl sulfoxide (DMSO), or a mixture thereof; in the presence of a phase transition catalysis such as kryptofix$_{2.2.2}$/potassium carbonate ($K_{2.2.2}$/$K_2CO_3$). Because the diaryliodonium salt precursors are unstable due to the radical production of their own in a heating or alkaline condition, were reacted in the presence of the radical scavenger 2,2,6,6-tetramethylpiperidine-1-oxyl (TEMPO). In a preferred method, the best result was obtained by reacting the compound of Formula (IB) in the presence of Kryptofix$_{2.2.2}$/potassium carbonate ($K_{2.2.2}$/$K_2CO_3$) under 2,2,6,6-tetramethylpiperidine-1-oxyl (TEMPO) in acetonitrile (ACN).

A compound of Formula (I) (as well as a compound of Formula (IA)) may be converted to their corresponding salts using methods known to one of ordinary skill in the art. For example, an amine of Formula (I) (as well as a compound of Formula (IA)) is treated with trifluoroacetic acid, HCl, or citric acid in a solvent such as diethyl ether ($Et_2O$), $CH_2Cl_2$, THF, methanol, chloroform, or isopropanol to provide the corresponding salt form.

Alternately, trifluoroacetic acid or formic acid salts are obtained as a result of reverse phase HPLC purification conditions. Crystalline forms of pharmaceutically acceptable salts of compounds of Formula (I) (as well as compounds of Formula (IA)) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Preparative reverse phase high performance liquid chromatography (RP-HPLC) was used to purify radioactive isotope labeled compounds using the following method: An internal HPLC attached to Synthra RNPlus module (Synthra GmbH, Germany) equipped with a Waters Xbridge C18 column (5 um, 10×250 mm), mobile phase of 10 mM $NH_4OAc$ and MeCN (50:50 v/v) at a flow rate of 4 mL/min, UV detection at 254 nm, internal radiation gamma detector.

Analytical RP-HPLC was used as quality control for radioactive isotope labelled compound. The following method was used: A Synthra (Synthra GmbH, Germany) HPLC with an Agilent Eclipse XDB-C$_{18}$ column (5 μm, 4.6 mm×150 mm) with a mobile phase of 5% ACN in water (0.05% TFA addition) was held for 1 min, then a gradient of 5-95% CAN over 10 min, then 95% CAN for 4 min, flow rate of 1 ml/min. UV detection was performed at 254 nm. The internal gamma detector was used for radiation measurement.

Mass spectra (MS) were obtained on an Agilent series 1260 infinity system. Electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, MA) or ACD/Name Version 10.01 (Advanced Chemistry).

Intermediate 1: (S)-3-(3,5-Difluorophenyl)-2,7-dimethyl-4,5,6,7-tetrahydro-2H-pyrazolo[3,4-c]pyridine hydrochloride.

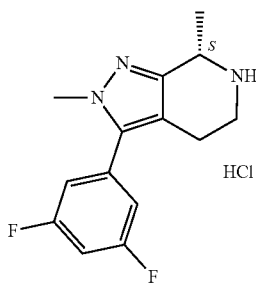

Method A:

Step A: 1-(tert-Butyl) 4-ethyl 2-methyl-3-oxopiperidine-1,4-dicarboxylate. To a cooled (−78° C.) solution of tert-butyl 2-methyl-3-oxopiperidine-1-carboxylate, (5 g, 23.4 mmol) in THF (35 mL), was added lithium bis(trimethylsilyl)amide (1.0 M in THF, 28.1 mL, 28.1 mmol) dropwise over a period of 10 minutes. Stirring was maintained at −78° C. for 30 minutes, and then a solution of ethyl cyanoformate (3.0 mL, 30.4 mmol) in THF (15 mL) was added dropwise at −78° C. over a period of 10 minutes. After the addition, the reaction mixture was then allowed to stir at same temperature (−78° C.) for 2 h. The reaction mixture was quenched with saturated aqueous $NH_4Cl$ and extracted with ethyl acetate (EtOAc) (2×100 mL). The combined organic extracts were dried over $Na_2SO_4$ and concentrated in vacuo. The resulting residue was purified by a flash chromatography (Silica gel; 0 to 30% EtOAc-hexanes) to afford the title compound as an oil (3.5 g, yield 52%). $^1$NMR (500 MHz, Chloroform-d): δ: 4.26-4.10 (m, 2H), 2.79 (s, 1H), 2.34-2.14 (m, 2H), 1.47 (d, J=27.0 Hz, 2H), 1.40 (s, 9H), 1.36 (s, 1H), 1.29 (d, J=6.9 Hz, 3H), 1.23 (t, J=7.1 Hz, 3H).

Step B: tert-Butyl 2,7-dimethyl-3-oxo-1,2,3,4,5,7-hexahydro-6H-pyrazolo[3,4-c]pyridine-6-carboxylate. To a solution of 1-(tert-butyl) 4-ethyl 2-methyl-3-oxopiperidine-1,4-dicarboxylate, (3.5 g, 12.1 mmol) in toluene (40.0 mL) was added methylhydrazine (0.96 mL, 18.1 mmol) and the resulting mixture was heated at 110° C. for 3 h. After cooling to rt, the solvent was concentrated in vacuo; the crude residue was purified by a flash chromatography (silica gel: 0 to 10% MeOH-DCM) to afford the title compound as an oil (2.7 g, yield 83%).

Step C: tert-Butyl 2,7-dimethyl-3-(((trifluoromethyl)sulfonyl)oxy)-2,4,5,7-tetrahydro-6H-pyrazolo[3,4-c]pyridine-6-carboxylate. To a solution of tert-butyl 2,7-dimethyl-3-oxo-1,2,3,4,5,7-hexahydro-6H-pyrazolo[3,4-c]pyridine-6-carboxylate, (2.7 g, 10.1 mmol) in DCM (45.0 mL) was added N,N-diisopropylethylamine (DIEA) (1.9 mL, 11.1 mmol) at rt. Addition of 1,1,1-trifluoro-N-phenyl-N-((trifluoromethyl)sulfonyl)methanesulfonamide (4.0 g, 11.1 mmol) was followed. The reaction mixture was stirred at rt for 5 h. The solvent was removed in vacuo; The crude residue was purified by flash chromatography (Silica gel; 0-20% EtOAc-hexanes, to give compound 4 as an oil (3.8 g, 86% yield).

The resultant racemic mixture was further purified via chiral SFC to obtain the desired 'S' enantiomer (tert-butyl (S)-2,7-dimethyl-3-(((trifluoromethyl)sulfonypoxy)-2,4,5,7-tetrahydro-6H-pyrazolo[3,4-c]pyridine-6-carboxylate), (1.84 g, yield 46%). The procedure of chiral separation is described in the section below. $^1$H NMR (500 MHz, Chloroform-d) δ: 5.23 (s, 1H), 4.25 (s, 1H), 3.70 (s, 3H), 2.85 (s, 1H), 2.47 (dtd, J=30.7, 15.4, 4.0 Hz, 2H), 1.41 (s, 9H), 1.34 (d, J=6.8 Hz, 3H).

Step D: (S)-3-(3,5-Difluorophenyl)-2,7-dimethyl-4,5,6,7-tetrahydro-2H-pyrazolo[3,4-c]pyridine hydrochloride. To a solution of tert-butyl (S)-2,7-dimethyl-3-(((trifluoromethyl)sulfonyl)oxy)-2,4,5,7-tetrahydro-6H-pyrazolo[3,4-c]pyridine-6- carboxylateethyl ester, (540 mg, 1.35 mmol), were added (3,5-difluorophenyl)boronic acid, (256 mg, 1.62 mmol), Xphos-Pd-G2 (106 mg, 0.135 mmol), sodium carbonate (1M aq, 4 ml, 4 mmol) and 1,4-dioxane (5 mL). The mixture was degassed with nitrogen for 5 mins, sealed and heated to 110° C. for one hour with stirring. The heating was removed. The mixture was stirred overnight at rt. The mixture was diluted with EtOAc (20 mL), washed with brine (30 mL). The organic layer was dried and concentrated. The residue was purified on a combi-flash silica gel column with EtOAc in hexanes (gradient 10% to 60%) to afford an oil product, (480 mg, yield 98%). MS (ESI): mass calcd. for $C_{19}H_{23}F_2N_3O_2$, 363.2; m/z found, 364.1 $[M+H]^+$. A suspension of the product from the first step (480 mg, 1.3 mmol) in DCM (8.5 mL) was treated with hydrochloric acid (4M, 1,4-dioxane, 3.3 ml, 13.2 mmol) at rt overnight. All solvents were removed under vacuum. The residue is an off-white solid, (404 mg, yield 102%) MS (ESI): mass calcd. for $C_{14}H_{16}ClF_2N_3$, 299.1; m/z found, 264.1 $[M-HCl+H]^+$. $^1$H NMR (DMSO-$d_6$): δ9.74 (s, 1H), 9.17 (br, 1H), 7.41 (m, 1H), 7.29-7.25 (m, 2H), 4.53 (s, 1H), 3.84 (s,3H), 3.70 (m, 1H), 3.20 (s, 1H), 2.88-2.77 (m, 2H), 1.58 (d, J=4.0, Hz, 3H).

Method B:

Step A: (E)-2-(3-(3,5-Difluorophenyl)-2-nitroallyl)-1,3-dioxolane. Dilute 2-(2-nitroethyl)-1,3-dioxolane (20.26 g, 137.72 mmol), 3,5-difluorobenzaldehyde (19.57 g, 137.72 mmol) and catalytic piperidine (2 mL, 20.25 mmol) in toluene (150 mL). Heat to reflux overnight. The reaction mixture was cooled to room temperature then quenched with saturated NaCl solution (150 mL). The extracted organic layer was dried with $Na_2SO_4$, filtered and concentrated to dark oil to recover quantitative crude yield of the title compound. The compound was used in the next step without further purification.

Step B: tert-Butyl (S,E)-(1-(2-methylhydrazineylidene)propan-2-yl)carbamate. A solution of methylhydrazine (3.04 mL, 57.73 mmol) and tert-butyl (S)-(1-oxopropan-2-yl) carbamate (10 g, 57.73 mmol) in THF (150 mL) was stirred for 4 hours at room temperature. The reaction mixture was dried over Na$_2$SO$_4$, filtered and evaporated under reduced pressure overnight. The title compound was isolated as a light oil in quantitative crude yield. The crude product was used in the next reaction without further purification.

Step C: tert-Butyl (S)-(1-(4-((1,3-dioxolan-2-yl)methyl)-5-(3,5-difluorophenyl)-1-methyl-1H-pyrazol-3-yl)ethyl)carbamate. To a solution of tert-Butyl (S,E)-(1-(2-methylhydrazineylidene)propan-2-yl)carbamate (11.62 g, 57.73 mmol) in EtOH (500 mL) was added (E)-2-(3-(3,5-difluorophenyl)-2-nitroallyl)-1,3-dioxolane (16.27 g, 59.98 mmol). The reaction was stirred overnight at room temperature under open air. The reaction mixture was mildly heated to 40° C. overnight to drive the reaction to completion. The reaction was concentrated to an oil then quenched with EtOAc (250 mL) and NaCl solution (250 mL). The extracted organic layer was washed with water then dried with Na$_2$SO$_4$, filtered and concentrated to dark orange oil. Purification (FCC, SiO$_2$, 7/3 hexane/EtOAc) afforded the title compound (13.32 g, 54.5%).

Step D: (S)-3-(3,5-Difluorophenyl)-2,7-dimethyl-4,5,6,7-tetrahydro-2H-pyrazolo[3,4-c]pyridine. A solution of tert-Butyl (S)-(1-(4-((1,3-dioxolan-2-yl)methyl)-5-(3,5-difluorophenyl)-1-methyl-1H-pyrazol-3-yl)ethyl)carbamate (4 g, 9.446 mmol) in CH$_2$Cl$_2$ (30 mL), TFA (8 mL, 104.54 mmol) and triethylsilane (23 mL, 144.0 mmol) was stirred for 30 minutes then heated to 55° C. overnight. The reaction mixture was concentrated to an oil then quenched with EtOAc and 1 N NaOH to pH 11-12. The extracted organic layer was dried with Na$_2$SO$_4$, filtered and evaporated to light brown oil. The crude product was diluted in EtOH and 1.1 equivalents of 1 N HCl (10 mL, 10 mmol) was added. The mixture was stirred over weekend without any formation of the HCl salt. The mixture was concentrated to a light brown solid then slurried in minimum 9/1 CH$_3$CN/TBME overnight. The solids were filtered to recover the HCl salt of the title compound (1.92 g, 68%).

Example 1: (S)-(2-Chloro-6-fluorophenyl)(3-(3,5-difluorophenyl)-2,7-dimethyl-2,4,5,7-tetrahydro-6H-pyrazolo[3,4-c]pyridin-6-yl)methanone

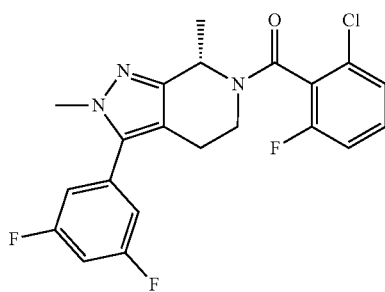 [SMILES: C[C@H]1c2nn(C)c(-c3cc(F)cc(F)c3)c2CCN1C(=O)c1c(F)cccc1Cl]

2-Chloro-6-fluorobenzoic acid, (20 mg, 0.12 mmol) and (S)-3-(3,5-difluorophenyl)-2,7-dimethyl-4,5,6,7-tetrahydro-2H-pyrazolo[3,4- c]pyridine hydrochloride (Intermediate 1, 20 mg, 0.076 mmol) were mixed in a solution of HATU (43.6 mg, 0.12 mmol) in DMF (0.6 mL). To the mixture, was added triethylamine (32 µL, 0.23 mmol) dropwise. The solution was stirred at rt for 0.5 hr. The mixture was diluted with EtOAc (15 mL), washed with NaHCO$_3$ (aq, 15 mL) and brine (15 mL). The organic layer was dried, filtered and concentrated under reduced pressure. Purification (FCC, SiO$_2$, EtOAc in hexanes, 10% to 70%) afforded the title compound as filmy oil (30 mg, 94%). MS (ESI): mass calcd. for C$_{21}$H$_{17}$ClF$_3$N$_3$O, 419.1; m/z found, 420.1 [M+H]$^{30}$. $^1$H NMR (CDCl3): δ7.34-7.18 (m, 2H), 7.12-6.98 (m, 1H), 6.90-6.84 (m, 3H), 5.95-5.91 and 5.01-4.98 (m, 1H), 4.76-4.69 and 3.57-3.50 (m, 1H), 3.86 and 3.80 (s, 3H), 3.39-3.30 and 3.11-3.03 (m, 1H), 2.86-2.73 and 2.69-2.63 (m, 1H), 2.53-2.49 and 2.39-2.35 (m, 1H), 1.63-1.56, 1.49 and 1.45 (m, 3H).

Example 2: (S)-(3-Chloro-2-(3-(3,5-difluorophenyl)-2,7-dimethyl-4,5,6,7-tetrahydro-2H-pyrazolo[3,4-c]pyridine-6-carbonyl)phenyl)(4-methoxyphenyl)iodonium trifluoromethanesulfonate.

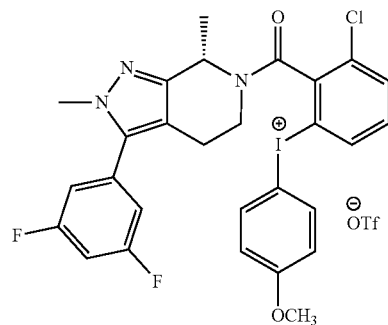 [SMILES: COc1ccc([I+]c2cccc(Cl)c2C(=O)N2CCc3c(nn(C)c3-c3cc(F)cc(F)c3)[C@@H]2C)cc1]

Step A: 2-Chloro-6-iodobenzoyl chloride. To a suspension of 2-chloro-6-iodobenzoic acid, (687 mg, 2.43 mmol) in DCM (5 mL), was added oxalyl chloride (550 mg, 4.33 mmol) at rt. To the reaction mixture was added 1 drop of DMF to accelerate the reaction. The reaction mixture was checked after stirring for 0.5 hr at rt. The mixture was concentrated under vacuum to a yellow oil and used in the next step without further purification.

Step B: (S)-(2-Chloro-6-iodophenyl)(3-(3,5-difluorophenyl)-2,7-dimethyl-2,4,5,7-tetrahydro-6H-pyrazolo[3,4-c]pyridin-6-yl)methanone. 2-Chloro-6-iodobenzoyl chloride (from Step A) was mixed with a solution of (S)-3-(3,5-difluorophenyl)-2,7-dimethyl-4,5,6,7-tetrahydro-2H-pyrazolo[3,4-c]pyridine hydrochloride (540 mg, 1.801 mmol) in DCM (10 mL) with triethylamine (626 µL, 4.5 mmol). The reaction mixture was stirred and allowed at rt overnight. The mixture was further diluted with DCM (30 mL), washed with brine (30 mL). The organic layers were dried, filtered and concentrated under reduced pressure. Purification (FCC, SiO$_2$, EtOAc in hexanes, 15% to 60%) afforded the title compound as a light-yellow oil (586 mg, 62%). MS (ESI): mass calcd. for C$_{21}$H$_{17}$ClF$_2$IN$_3$O, 527.0; m/z found, 528.0 [M+H]+. $^1$H NMR (CDCl$_3$): δ7.81-7.67 (m, 1H), 7.44-7.32 (m, 1H), 6.97-6.92 (m, 1H), 6.83-6.77 (m, 3H), 5.87-5.80 (m, 1H), 3.79 (s, 3H), 3.43-3.36 (m, 1H), 3.33-3.24 (m, 1H), 2.91-2.70 (m, 1H), 2.32-2.26 (m, 1H), 1.61 and 1.57 (d, J=6.8 Hz, 3H).

Step C: (S)-(3-Chloro-2-(3-(3,5-difluorophenyl)-2,7-dimethyl-4,5,6,7-tetrahydro-2H-pyrazolo[3,4-c]pyridine-6-carbonyl)phenyl)(4- methoxyphenyl)iodonium trifluoromethanesulfonate. To a cooled solution (−15~20° C. in a sodium chloride-ice bath) of (S)-(2-chloro-6-iodophenyl)(3-(3,5-difluorophenyl)-2,7-dimethyl-2,4,5,7-tetrahydro-6H-pyrazolo[3,4-c]pyridin-6-yl)methanone (140 mg, 0.265 mmol) in DCM (anhydrous, 1 mL) was added trifluorosulfonic acid (94 µL, 1.06 mmol) dropwise without disturbing temperature. After 10 min, a suspension of meta-chloroperoxybenzoic acid (m-CPBA) (max 77%, 148 mg, 0.663 mmol) in DCM (0.7 mL) was added to the solution slowly. The reaction mixture was stirred at −20° C. for additional 30 min, then the cooling was removed, and the temperature was increased to rt. The reaction mixture was stirred at room temperature for 16. The reaction mixture was cooled in an ice bath. To the reaction mixture was added water (10 µL, 0.53 mmol) then anisole (43 mg, 0.398 mmol) was added. The ice bath was removed, and the reaction mixture was stirred at rt for another 2 hrs. The reaction mixture was concentrated under reduced pressure. Diethyl ether (5 mL) was added to the crude concentrated reaction mixture, and the resulting mixture was sonicated and filtered. The solid crude product was collected as an off-yellow wax after drying overnight (~200 mg). Purification (FCC, alumina column (purged with DCM), eluted carefully with DCM, then 10% MeOH/DCM) afforded the title compound as an off-white solid. The title compound was re-dissolved in acetonitrile (20 mg/mL) and filtered through a 0.45 µm syringe filter and the resulting solution was concentrated under reduced pressure. Diethyl ether was added to the resulting solution to precipitate the title compound (140 mg, 67%). MS (ESI): mass calcd. for $C_{29}H_{24}ClF_5IN_3O_5S$, 783.0; m/z found, 633.9 $[M-OTf]^+$. $^1H$ NMR (DMSO-$d_6$): δ8.58 (m, 1H), 8.13-8.07 (m, 2H), 7.90-7.86 (m, 1H), 7.67-7.58 (m, 1H), 7.38-7.17 (m, 3H), 7.10 (m, 1H), 7.02 (m, 1H), 5.73-5.58 (m, 1H), 3.87-3.74 (m, 6H), 3.45-3.19 (m, 2H), 2.92-2.63 (m, 1H), 2.43-2.29 (m, 1H), 1.63-1.51 (m, 3H).

Example 3: (S)-(2-Chloro-6-($^{18}$F)fluoro-)phenyl)(3-(3,5-difluorophenyl)-2,7-dimethyl-2,4,5,7-tetrahydro-6H-pyrazolo[3,4-c]pyridin-6-yl)methanone

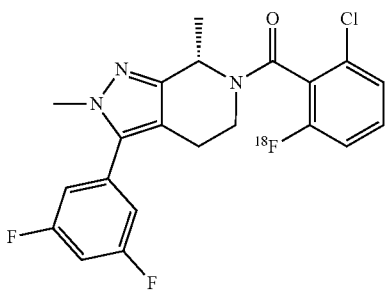 [SMILES: C[C@H]1c2nn(C)c(-c3cc(F)cc(F)c3)c2CCN1C(=O)c1c([18F])cccc1Cl]

In a typical procedure, [18F]fluoride in a shipping vial (obtained from the cyclotron facility) is transferred onto and trapped on an ion exchange cartridge. It is then eluted into the reaction vessel (RV1) of the Synthra RNPlus® module with a solution of potassium carbonate (0.75 mg, 5.4 umol) and Kryptofix 222 (7.2 mg, 19.2 umol) in acetonitrile/water (0.8 mL, 6/2, v/v). After the solvent was evaporated under a stream of nitrogen at 85° C. and under vacuum, anhydrous CH$_3$CN (0.5 mL) was added, this process was repeated, and the temperature increased to 110° C. for 3.5 min. The reaction vial was then cooled to 70° C. before a solution of (S)-(3-chloro-2-(3-(3,5-difluorophenyl)-2,7-dimethyl-4,5,6,7-tetrahydro-2H-pyrazolo[3,4-c]pyridine-6-carbonyl)phenyl)(4- methoxyphenyl)iodonium trifluoromethanesulfonate (Example 2, 15.0 mg, 19.1 umol) and TEMPO (4.4 mg, 28.1 umol) in anhydrous acetonitrile (0.7 mL) was added to the reaction vessel. The reaction mixture was heated at 125° C. for 10 min. The reactor was cooled to 40° C. and diluted with water (4.3 mL) and the contents is transferred into the HPLC injector loop for purification.

Purification is performed by HPLC using a semi-preparative Eclipse XDB-C18 column (5 µm, 9.4 mm×250 mm) with a mixture of 10 mM NH$_4$OAc and MeCN (50:50 v/v) at a flow rate of 4 mL/min with UV detection at 254 nm. The purified radiotracer solution was diluted with 30 mL of water and passed through a SepPak Light C-18 cartridge. The C-18 cartridge was further washed with 10 mL of water before 0.5 mL EtOH was used to elute the tracer. The tracer solution was further diluted with 4.5 mL of saline. The final formulation contains an ethanol concentration of 10%, suitable for intravenous injection (i.v.).

Quality control testing includes identity, chemical, and radiochemical purity by HPLC using an Eclipse XDB C18 (5 µm, 4.6×250 mm) column eluted with a mixture of 0.05% TFA solution and MeCN at a flow rate of 1 mL/min equipped with serial UV (254 nm) and gamma detection.

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15;318(2):270-5.). The assay consists of combining endogenously expressed MGL from HeLa cells with test compounds, adding [glycerol-1,3-$^3$H]-oleyl glycerol, incubating for one hour, and then measuring the amount of cleaved [1,3-$^3$H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-$^3$H]-oleyl glycerol with human MGL from HeLa cells and test compounds for one hour, after which the reaction is filtered through activated carbon and tritium is measured in the flow through. The test compound concentration in screening mode is 10 uM, while the highest compound concentration in IC$_{50}$ assays is determined empirically. MGL is the predominant hydrolase in HeLa cells/cell homogenates. The results of testing the compound prepared according to Example 1 is set forth below in Table 2:

TABLE 2

| Ex # | Compound Name | MGL IC$_{50}$ (nM) |
|---|---|---|
| 1 | (S)-(2-Chloro-6-fluorophenyl)(3-(3,5-difluorophenyl)-2,7-dimethyl-2,4,5,7-tetrahydro-6H-pyrazolo[3,4-c]pyridin-6-yl)methanone; | 0.0023 |
| 3 | (S)-(2-Chloro-6-($^{18}$F)fluoro-)phenyl)(3-(3,5-difluorophenyl)-2,7-dimethyl-2,4,5,7-tetrahydro-6H-pyrazolo[3,4-c]pyridin-6-yl)methanone. | NT |

NT indicates not tested.

Figure 2:
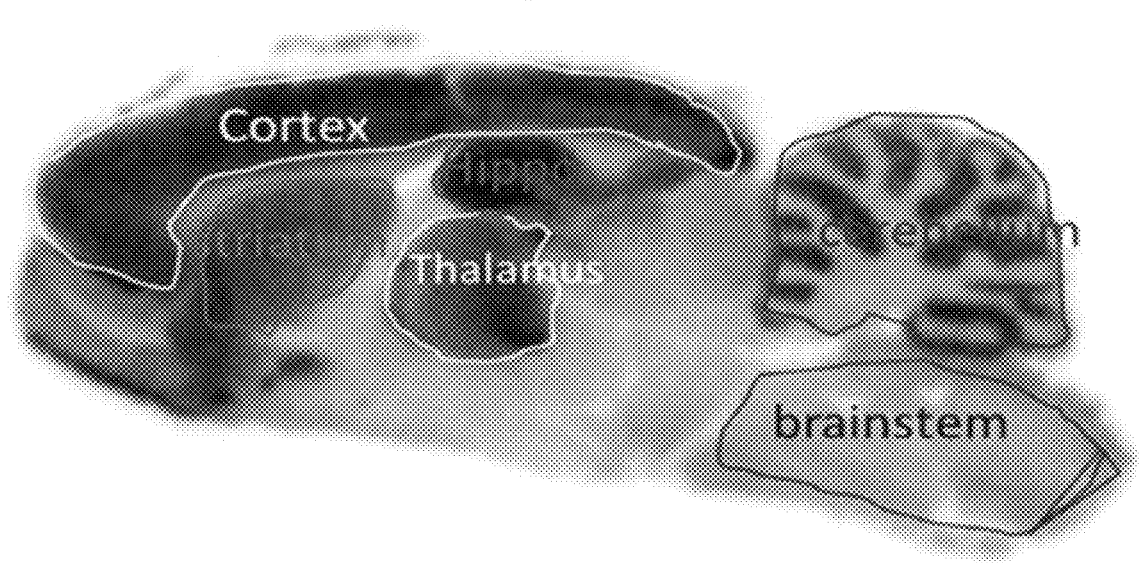
FIG. 2. Autoradiography (ARG) of the compound of Example 3 on normal rat brain sections which was cut adjacent to the section used for IHC staining in FIG. 1 (sagittal view)

Example 4: Autoradiography of (S)-(2-Chloro-6-(18F)fluoro-)phenyl)(3-(3,5-difluorophenyl)-2,7-dimethyl-2,4,5,7-tetrahydro-6H-pyrazolo[3,4-c]pyridin-6- yl)methanone (Example 3) and Comparison to IHC Staining of MGL Using Adjacent Rat Brain Section In vitro ARG using the compound of Example 3 was performed on a frozen normal rat brain sections (sagittal cut, thickness at 20 um). After taken out from freezer for 15 min, the rat brain section was added 250 ul of buffer solution (50 mM Tris-HCl pH=7.4) which contains the compound of Example 3 with the concentration of 400 uCi/ml. The brain section was incubated with the incubation buffer at room temperature for 30 min, was then washed with blank fresh buffer solution for 5 min, repeated 3 times. The brain section was air-dried, exposed to a phosphor screen in a cassette in dark environment for 18 hours. The screen was then scanned then Typhoon™ FLA 7000 Image Analyzer (GE) to generate the autoradiography of the compound of Example 3 on rat brain section (FIG. 2). ARG signals was found high in hippocampus, cortex, cerebellum and thalamus regions and low in brainstem. The distribution pattern matches IHC staining pattern described below.

The IHC staining was performed on a frozen normal rat brain section (sagittal cut, thickness at 10 um) which is adjacent to the brain section used in ARG described above. After taken out from freezer for 15 min, the rat brain section was added 4% paraformaldehyde and fixed for 20 min at room temperature. The section was then washed with fresh phosphate buffer solution (PBS, 0.01 M, pH=7.4) for 5 min, repeated 3 times, followed by treatment of hydrogen peroxide solution (3% in PBS) at room temperature for 20 min. 10% goat serum (Simga #G-9023) in PBS was added to the section to block non-specific binding. Primary antibody MGL antibody (Novus Biologicals, Cat #NBP2-19389) in PBS (1:100 dilution) was added, incubated at 4° C. overnight in a humid chamber. The second day, the rat brain section was washed with PBS for 10 min, repeated 3 times. The secondary antibody goat anti-rabbit IgG (H+L) antibody (ThermoFisher #A-11008) was added in PBS (dilution 1:500) and incubated for 1 h at room temperature. The section was further washed with PBS for 10 min, repeated 3 times, covered by slide with mounting medium and observed under a fluorescent microscope. The picture (FIG. 1) was taken using the fluorescent microscope (Zeiss, AXIO, Imager M2). The IHC staining indicated MGL distributes high in hippocampus, cortex, and cerebellum, this pattern matches autoradiography signal described above.

The invention claimed is:

1. A method of imaging a tissue, cells or a host, comprising contacting with or administering to a tissue, cells or a host, a compound according to Formula (VIII)

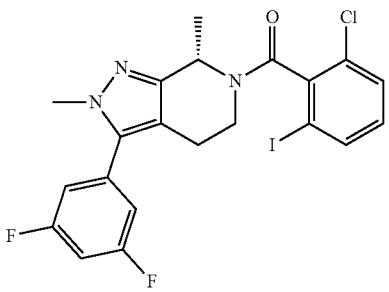

or a pharmaceutically acceptable salt thereof.

2. A method of imaging a tissue, cells or a host, comprising contacting with or administering to a tissue, cells or a host, a compound according to Formula (IB)

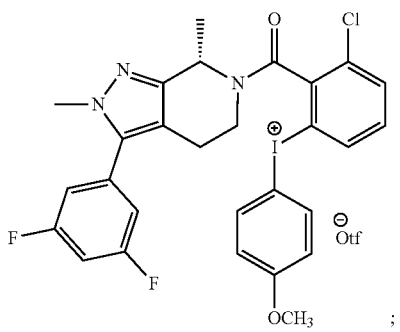

or a pharmaceutically acceptable salt thereof.

3. The method according to claim 1, wherein the compound of Formula (VIII) is used in imaging a tissue, cells or a host, in vitro or in vivo.

4. The method according to claim 1, wherein the compound of Formula (VIII) is in a steril solution.

* * * * *